United States Patent
Hatlestad et al.

(10) Patent No.: US 8,002,553 B2
(45) Date of Patent: Aug. 23, 2011

(54) SLEEP QUALITY DATA COLLECTION AND EVALUATION

(75) Inventors: John D. Hatlestad, Maplewood, MN (US); Quan Ni, Shoreview, MN (US); Jeffrey E. Stahmann, Ramsey, MN (US); Jesse Hartley, Lino Lakes, MN (US); Qingsheng Zhu, Little Canada, MN (US); Bruce H. Kenknight, Maple Grove, MN (US); Douglas R. Daum, Oakdale, MN (US); Kent Lee, Fridley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 814 days.

(21) Appl. No.: 10/642,998

(22) Filed: Aug. 18, 2003

(65) Prior Publication Data

US 2005/0042589 A1 Feb. 24, 2005

(51) Int. Cl.
*G09B 23/28* (2006.01)
(52) U.S. Cl. .................................. 434/262; 600/300
(58) Field of Classification Search .......... 340/575–576; 600/26, 300, 587, 595, 544, 28; 434/262–275; 128/630, 670–671, 716, 731, 733; 446/83
See application file for complete search history.

(56) References Cited

U.S. PATENT DOCUMENTS

| | | | |
|---|---|---|---|
| 3,650,277 A | 3/1972 | Sjostrand et al. | |
| 4,091,818 A | 5/1978 | Brownlee et al. | |
| 4,312,355 A | 1/1982 | Funke | |
| 4,312,734 A | 1/1982 | Nichols | |
| 4,365,636 A | 12/1982 | Barker | |
| 4,390,405 A | 6/1983 | Hahn et al. | |
| 4,414,982 A | 11/1983 | Durkan | |
| 4,648,407 A | 3/1987 | Sackner | |
| 4,702,253 A | 10/1987 | Nappholz et al. | |
| 4,721,110 A | 1/1988 | Lampadius | |
| 4,777,962 A | 10/1988 | Watson et al. | |
| 4,784,162 A | 11/1988 | Ricks et al. | |
| 4,791,931 A | 12/1988 | Slate | |
| 4,802,485 A | 2/1989 | Bowers et al. | |
| 4,807,629 A | 2/1989 | Baudino et al. | |
| 4,813,427 A | 3/1989 | Schlaefke et al. | |
| 4,827,943 A | 5/1989 | Bornn et al. | |

(Continued)

FOREIGN PATENT DOCUMENTS

EP 0547734 6/1993

(Continued)

OTHER PUBLICATIONS

"Aircraft Noise and Sleep Disturbance: final report"; Aug. 1980; Department of Trade; retrieved from http://www.caa.co.uk/docs/33/ERCD%208008.pdf.*

(Continued)

*Primary Examiner* — Xuan M Thai
*Assistant Examiner* — Timothy Musselman
(74) *Attorney, Agent, or Firm* — Hollingsworth & Funk, LLC

(57) ABSTRACT

A sleep quality assessment approach involves collecting data based on detected physiological or non-physiological patient conditions. At least one of detecting patient conditions and collecting data is performed using an implantable device. Sleep quality may be evaluated using the collected data by an implantable or patient-external sleep quality processor. One approach to sleep quality evaluation involves computing one or more summary metrics based on occurrences of movement disorders or breathing disorders during sleep.

25 Claims, 22 Drawing Sheets

U.S. PATENT DOCUMENTS

| | | | |
|---|---|---|---|
| 4,830,008 A | 5/1989 | Meer | |
| 4,836,219 A | 6/1989 | Hobson et al. | |
| 4,856,524 A | 8/1989 | Baker, Jr. | |
| 4,860,766 A | 8/1989 | Sackner | |
| 4,875,477 A | 10/1989 | Waschke et al. | |
| 4,886,064 A | 12/1989 | Strandberg | |
| 4,953,551 A | 9/1990 | Mehra et al. | |
| 4,958,632 A | 9/1990 | Duggan | |
| 4,961,423 A | 10/1990 | Canducci | |
| 4,972,842 A | 11/1990 | Korten et al. | |
| 4,982,738 A | 1/1991 | Griebel | |
| 5,003,975 A | 4/1991 | Hafelfinger et al. | |
| 5,010,888 A | 4/1991 | Jadvar et al. | |
| 5,024,222 A | 6/1991 | Thacker | |
| 5,047,930 A | 9/1991 | Martens et al. | |
| 5,063,927 A | 11/1991 | Webb et al. | |
| 5,074,301 A | 12/1991 | Gill | |
| 5,101,831 A | 4/1992 | Koyama et al. | |
| 5,111,815 A | 5/1992 | Mower | |
| 5,123,425 A | 6/1992 | Shannon, Jr. et al. | |
| 5,133,353 A | 7/1992 | Hauser | |
| 5,146,918 A * | 9/1992 | Kallok et al. | 607/2 |
| 5,156,157 A | 10/1992 | Valenta, Jr. et al. | |
| 5,158,089 A | 10/1992 | Swezey et al. | |
| 5,170,784 A | 12/1992 | Ramon et al. | |
| 5,174,287 A | 12/1992 | Kallok et al. | |
| 5,179,945 A | 1/1993 | Van Hofwegen et al. | |
| 5,183,038 A | 2/1993 | Hoffman et al. | |
| 5,188,106 A | 2/1993 | Nappholz et al. | |
| 5,190,035 A | 3/1993 | Salo et al. | |
| 5,199,424 A | 4/1993 | Sullivan et al. | |
| 5,199,428 A | 4/1993 | Obel et al. | |
| 5,203,326 A | 4/1993 | Collins | |
| 5,209,229 A | 5/1993 | Gilli | |
| 5,211,173 A | 5/1993 | Kallok et al. | |
| 5,215,082 A | 6/1993 | Kallok et al. | |
| 5,233,983 A | 8/1993 | Markowitz | |
| 5,243,979 A | 9/1993 | Stein et al. | |
| 5,243,980 A | 9/1993 | Mehra | |
| 5,245,995 A * | 9/1993 | Sullivan et al. | 128/204.23 |
| 5,259,373 A | 11/1993 | Gruenke et al. | |
| 5,261,400 A | 11/1993 | Bardy | |
| 5,275,159 A | 1/1994 | Griebel | |
| 5,280,791 A | 1/1994 | Lavie | |
| 5,292,338 A | 3/1994 | Bardy | |
| 5,299,118 A | 3/1994 | Martens et al. | |
| 5,300,106 A | 4/1994 | Dahl et al. | |
| 5,306,293 A | 4/1994 | Zacouto | |
| 5,314,430 A | 5/1994 | Bardy | |
| 5,314,459 A | 5/1994 | Swanson et al. | |
| 5,318,592 A | 6/1994 | Schaldach | |
| 5,318,593 A | 6/1994 | Duggan | |
| 5,318,594 A | 6/1994 | Limousin et al. | |
| 5,318,597 A | 6/1994 | Hauck et al. | |
| 5,330,505 A | 7/1994 | Cohen | |
| 5,330,507 A | 7/1994 | Schwartz | |
| 5,331,966 A | 7/1994 | Bennett et al. | |
| 5,334,221 A | 8/1994 | Bardy | |
| 5,353,788 A | 10/1994 | Miles | |
| 5,356,425 A | 10/1994 | Bardy et al. | |
| 5,363,842 A | 11/1994 | Mishelevich et al. | |
| 5,372,606 A | 12/1994 | Lang et al. | |
| 5,376,103 A | 12/1994 | Anderson et al. | |
| 5,376,106 A | 12/1994 | Stahmann et al. | |
| 5,377,671 A | 1/1995 | Biondi et al. | |
| 5,391,187 A | 2/1995 | Freeman | |
| 5,398,682 A | 3/1995 | Lynn | |
| 5,404,877 A | 4/1995 | Nolan et al. | |
| 5,411,525 A | 5/1995 | Swanson et al. | |
| 5,411,531 A | 5/1995 | Hill et al. | |
| 5,411,539 A | 5/1995 | Neisz | |
| 5,417,717 A | 5/1995 | Salo et al. | |
| 5,437,285 A | 8/1995 | Verrier et al. | |
| 5,439,482 A | 8/1995 | Adams et al. | |
| 5,441,518 A | 8/1995 | Adams et al. | |
| 5,466,245 A | 11/1995 | Heemels et al. | |
| 5,468,254 A | 11/1995 | Hahn et al. | |
| 5,476,485 A | 12/1995 | Weinberg et al. | |
| 5,483,969 A | 1/1996 | Testerman et al. | |
| 5,485,851 A | 1/1996 | Erickson | |
| 5,487,755 A | 1/1996 | Snell et al. | |
| 5,490,502 A | 2/1996 | Rapoport et al. | |
| 5,507,784 A | 4/1996 | Hill et al. | |
| 5,517,983 A | 5/1996 | Deighan et al. | |
| 5,520,176 A * | 5/1996 | Cohen | 600/300 |
| 5,520,191 A | 5/1996 | Karlsson et al. | |
| 5,522,382 A | 6/1996 | Sullivan et al. | |
| 5,522,854 A | 6/1996 | Ideker et al. | |
| 5,522,862 A | 6/1996 | Testerman et al. | |
| 5,527,345 A | 6/1996 | Infinger | |
| 5,531,779 A | 7/1996 | Dahl et al. | |
| 5,540,732 A | 7/1996 | Testerman | |
| 5,540,734 A | 7/1996 | Zabara | |
| 5,554,177 A | 9/1996 | Kieval | |
| 5,578,061 A | 11/1996 | Stroetmann et al. | |
| 5,590,648 A | 1/1997 | Mitchell et al. | |
| 5,591,216 A | 1/1997 | Testerman et al. | |
| 5,593,431 A | 1/1997 | Sheldon | |
| 5,601,607 A | 2/1997 | Adams | |
| 5,603,331 A | 2/1997 | Heemels et al. | |
| 5,605,151 A | 2/1997 | Lynn | |
| 5,606,969 A | 3/1997 | Butler et al. | |
| 5,607,385 A | 3/1997 | Francischelli et al. | |
| 5,620,466 A | 4/1997 | Haefner et al. | |
| 5,622,178 A | 4/1997 | Gilham | |
| 5,626,151 A | 5/1997 | Linden | |
| 5,632,281 A | 5/1997 | Rayburn | |
| 5,634,938 A | 6/1997 | Swanson et al. | |
| 5,641,326 A | 6/1997 | Adams | |
| 5,645,570 A | 7/1997 | Corbucci | |
| 5,658,318 A | 8/1997 | Stroetmann et al. | |
| 5,662,688 A | 9/1997 | Haefner et al. | |
| 5,690,681 A | 11/1997 | Geddes et al. | |
| 5,693,000 A | 12/1997 | Crosby et al. | |
| 5,697,951 A | 12/1997 | Harpstead et al. | |
| 5,697,953 A | 12/1997 | Kroll et al. | |
| 5,700,282 A | 12/1997 | Zabara | |
| 5,701,894 A | 12/1997 | Cherry et al. | |
| 5,704,345 A | 1/1998 | Berthon-Jones | |
| 5,704,365 A | 1/1998 | Albrecht et al. | |
| 5,707,400 A | 1/1998 | Terry, Jr. et al. | |
| 5,713,355 A | 2/1998 | Richardson et al. | |
| 5,713,933 A | 2/1998 | Condie et al. | |
| 5,715,812 A | 2/1998 | Deighan et al. | |
| 5,716,377 A | 2/1998 | Rise et al. | |
| 5,720,771 A | 2/1998 | Snell | |
| 5,724,984 A | 3/1998 | Arnold et al. | |
| 5,740,797 A | 4/1998 | Dickson | |
| 5,782,883 A | 7/1998 | Kroll et al. | |
| 5,792,188 A | 8/1998 | Starkweather et al. | |
| 5,794,615 A | 8/1998 | Estes | |
| 5,797,967 A | 8/1998 | KenKnight | |
| 5,800,470 A | 9/1998 | Stein et al. | |
| 5,802,188 A | 9/1998 | McDonough | |
| 5,814,079 A | 9/1998 | Kieval | |
| 5,826,579 A | 10/1998 | Remmers et al. | |
| 5,827,326 A | 10/1998 | Kroll et al. | |
| 5,839,430 A | 11/1998 | Cama | |
| 5,844,680 A | 12/1998 | Sperling | |
| 5,860,918 A | 1/1999 | Schradi et al. | |
| 5,861,011 A | 1/1999 | Stoop | |
| 5,869,970 A | 2/1999 | Palm et al. | |
| 5,876,353 A | 3/1999 | Riff | |
| 5,891,023 A | 4/1999 | Lynn | |
| 5,895,414 A | 4/1999 | Sanchez-Zambrano | |
| 5,902,250 A | 5/1999 | Verrier et al. | |
| 5,911,218 A | 6/1999 | DiMarco | |
| 5,916,239 A | 6/1999 | Geddes et al. | |
| 5,919,141 A | 7/1999 | Money et al. | |
| 5,957,861 A | 9/1999 | Combs et al. | |
| 5,957,956 A | 9/1999 | Kroll et al. | |
| 5,961,446 A | 10/1999 | Beller et al. | |
| 5,961,450 A | 10/1999 | Merchant et al. | |
| 5,964,788 A | 10/1999 | Greenhut | |
| 5,970,975 A | 10/1999 | Estes et al. | |
| 5,974,340 A | 10/1999 | Kadhiresan | |
| 5,974,349 A | 10/1999 | Levine | |

| | | | |
|---|---|---|---|
| 5,981,011 A | 11/1999 | Overcash et al. | |
| 5,997,526 A | 12/1999 | Giba et al. | |
| 6,006,134 A | 12/1999 | Hill et al. | |
| 6,015,388 A | 1/2000 | Sackner et al. | |
| 6,021,351 A | 2/2000 | Kadhiresan et al. | |
| 6,044,297 A | 3/2000 | Sheldon et al. | |
| 6,045,513 A | 4/2000 | Stone et al. | |
| 6,047,203 A | 4/2000 | Sackner et al. | |
| 6,050,940 A | 4/2000 | Braun et al. | |
| 6,058,331 A | 5/2000 | King | |
| 6,059,725 A * | 5/2000 | Steinschneider | 600/300 |
| 6,064,910 A | 5/2000 | Andersson et al. | |
| 6,073,048 A | 6/2000 | Kieval et al. | |
| 6,091,986 A | 7/2000 | Keimel | |
| 6,099,479 A | 8/2000 | Christopherson et al. | |
| 6,105,575 A | 8/2000 | Estes et al. | |
| 6,115,628 A | 9/2000 | Stadler et al. | |
| 6,117,092 A | 9/2000 | Weinstein et al. | |
| 6,120,441 A | 9/2000 | Griebel | |
| 6,134,470 A | 10/2000 | Hartlaub | |
| 6,141,590 A | 10/2000 | Renirie et al. | |
| 6,144,866 A | 11/2000 | Miesel et al. | |
| 6,148,230 A | 11/2000 | KenKnight | |
| 6,148,233 A | 11/2000 | Owen et al. | |
| 6,148,814 A | 11/2000 | Clemmer et al. | |
| 6,155,976 A | 12/2000 | Sackner et al. | |
| 6,161,042 A | 12/2000 | Hartley et al. | |
| 6,168,568 B1 | 1/2001 | Gavriely | |
| 6,178,349 B1 | 1/2001 | Kieval | |
| 6,181,961 B1 | 1/2001 | Prass | |
| 6,181,966 B1 | 1/2001 | Nigam | |
| 6,200,265 B1 * | 3/2001 | Walsh et al. | 600/300 |
| 6,205,357 B1 | 3/2001 | Ideker et al. | |
| 6,212,435 B1 | 4/2001 | Lattner et al. | |
| 6,227,072 B1 | 5/2001 | Ritchey et al. | |
| 6,236,873 B1 | 5/2001 | Holmström | |
| 6,240,314 B1 | 5/2001 | Plicchi et al. | |
| 6,240,316 B1 | 5/2001 | Richmond et al. | |
| 6,253,103 B1 | 6/2001 | Baura | |
| 6,261,238 B1 | 7/2001 | Gavriely | |
| 6,263,244 B1 | 7/2001 | Mann et al. | |
| 6,264,606 B1 | 7/2001 | Ekwall et al. | |
| 6,269,269 B1 | 7/2001 | Ottenhoff et al. | |
| 6,270,457 B1 | 8/2001 | Bardy | |
| 6,275,727 B1 | 8/2001 | Hopper et al. | |
| 6,280,462 B1 | 8/2001 | Hauser et al. | |
| 6,286,508 B1 | 9/2001 | Remmers et al. | |
| 6,287,264 B1 | 9/2001 | Hoffman | |
| 6,292,693 B1 | 9/2001 | Darvish et al. | |
| 6,292,695 B1 | 9/2001 | Webster et al. | |
| 6,299,581 B1 | 10/2001 | Rapoport et al. | |
| 6,303,270 B1 | 10/2001 | Flaim et al. | |
| 6,306,088 B1 | 10/2001 | Krausman | |
| 6,310,085 B1 | 10/2001 | Willis | |
| 6,312,378 B1 | 11/2001 | Bardy | |
| 6,314,319 B1 | 11/2001 | Kroll et al. | |
| 6,317,627 B1 | 11/2001 | Ennen | |
| 6,327,499 B1 | 12/2001 | Alt | |
| 6,331,536 B1 | 12/2001 | Radulovacki et al. | |
| 6,336,903 B1 | 1/2002 | Bardy | |
| 6,351,670 B1 | 2/2002 | Kroll | |
| 6,357,444 B1 | 3/2002 | Parker | |
| 6,360,127 B1 | 3/2002 | Ding et al. | |
| 6,361,494 B1 * | 3/2002 | Lindenthaler | 600/373 |
| 6,361,522 B1 | 3/2002 | Scheiner et al. | |
| 6,366,813 B1 | 4/2002 | DiLorenzo | |
| 6,375,614 B1 | 4/2002 | Braun et al. | |
| 6,375,623 B1 | 4/2002 | Gavriely | |
| 6,387,907 B1 | 5/2002 | Hendricks et al. | |
| 6,397,845 B1 | 6/2002 | Burton | |
| 6,398,727 B1 | 6/2002 | Bui et al. | |
| 6,398,728 B1 * | 6/2002 | Bardy | 600/300 |
| 6,398,739 B1 | 6/2002 | Sullivan et al. | |
| 6,400,982 B2 | 6/2002 | Sweeney et al. | |
| 6,409,675 B1 | 6/2002 | Turcott | |
| 6,411,845 B1 | 6/2002 | Mower et al. | |
| 6,411,850 B1 | 6/2002 | Kay et al. | |
| 6,414,183 B1 | 7/2002 | Sakamoto et al. | |
| 6,415,174 B1 | 7/2002 | Bebehani et al. | |
| 6,415,183 B1 | 7/2002 | Scheiner et al. | |
| 6,421,557 B1 | 7/2002 | Meyer | |
| 6,431,171 B1 | 8/2002 | Burton | |
| 6,438,407 B1 | 8/2002 | Ousdigian et al. | |
| 6,442,413 B1 | 8/2002 | Silver | |
| 6,442,433 B1 | 8/2002 | Linberg | |
| 6,447,459 B1 | 9/2002 | Larom | |
| 6,449,503 B1 | 9/2002 | Hsu | |
| 6,449,507 B1 | 9/2002 | Hill et al. | |
| 6,450,957 B1 | 9/2002 | Yoshimi | |
| 6,454,708 B1 | 9/2002 | Ferguson et al. | |
| 6,454,719 B1 | 9/2002 | Greenhut | |
| 6,463,326 B1 | 10/2002 | Hartley et al. | |
| 6,467,333 B2 | 10/2002 | Lewis et al. | |
| 6,468,219 B1 | 10/2002 | Njemanze | |
| 6,473,644 B1 | 10/2002 | Terry, Jr. et al. | |
| 6,477,420 B1 | 11/2002 | Struble et al. | |
| 6,487,450 B1 | 11/2002 | Chen et al. | |
| 6,491,639 B1 | 12/2002 | Turcott | |
| 6,493,585 B2 | 12/2002 | Plicchi et al. | |
| 6,496,715 B1 | 12/2002 | Lee et al. | |
| 6,497,658 B2 | 12/2002 | Roizen et al. | |
| 6,505,067 B1 | 1/2003 | Lee et al. | |
| 6,511,500 B1 | 1/2003 | Rahme | |
| 6,512,940 B1 | 1/2003 | Brabec et al. | |
| 6,514,218 B2 | 2/2003 | Yamamoto | |
| 6,522,915 B1 | 2/2003 | Ceballos et al. | |
| 6,522,926 B1 | 2/2003 | Kieval et al. | |
| 6,527,729 B1 | 3/2003 | Turcott | |
| 6,532,388 B1 | 3/2003 | Hill et al. | |
| 6,542,774 B2 | 4/2003 | Hill et al. | |
| 6,544,199 B1 | 4/2003 | Morris | |
| 6,547,743 B2 | 4/2003 | Brydon | |
| 6,564,096 B2 | 5/2003 | Mest | |
| 6,564,106 B2 | 5/2003 | Guck et al. | |
| 6,572,543 B1 | 6/2003 | Christopherson et al. | |
| 6,580,944 B1 | 6/2003 | Katz et al. | |
| 6,584,351 B1 | 6/2003 | Ekwall | |
| 6,595,927 B2 | 7/2003 | Pitts-Crick et al. | |
| 6,595,928 B2 | 7/2003 | Mansy et al. | |
| 6,600,949 B1 | 7/2003 | Turcott | |
| 6,606,993 B1 | 8/2003 | Wiesmann et al. | |
| 6,607,509 B2 | 8/2003 | Bobroff et al. | |
| 6,611,713 B2 | 8/2003 | Schauerte | |
| 6,615,083 B2 | 9/2003 | Kupper | |
| 6,618,618 B2 | 9/2003 | Kalgren et al. | |
| 6,622,041 B2 | 9/2003 | Terry, Jr. et al. | |
| 6,622,046 B2 | 9/2003 | Fraley et al. | |
| 6,628,986 B1 | 9/2003 | Mouchawar et al. | |
| 6,628,987 B1 | 9/2003 | Hill et al. | |
| 6,641,542 B2 * | 11/2003 | Cho et al. | 600/529 |
| 6,658,292 B2 | 12/2003 | Kroll et al. | |
| 6,662,032 B1 | 12/2003 | Gavish et al. | |
| 6,679,250 B2 | 1/2004 | Walker et al. | |
| 6,694,186 B2 | 2/2004 | Bardy | |
| 6,704,590 B2 | 3/2004 | Haldeman | |
| 6,708,058 B2 | 3/2004 | Kim et al. | |
| 6,723,055 B2 | 4/2004 | Hoffman | |
| 6,731,984 B2 | 5/2004 | Cho et al. | |
| 6,741,885 B1 | 5/2004 | Park et al. | |
| 6,748,252 B2 | 6/2004 | Lynn et al. | |
| 6,752,765 B1 | 6/2004 | Jensen et al. | |
| 6,752,766 B2 | 6/2004 | Kowallik et al. | |
| 6,760,615 B2 | 7/2004 | Ferek-Petric | |
| 6,766,190 B2 | 7/2004 | Ferek-Petric | |
| 6,770,029 B2 | 8/2004 | Iliff | |
| 6,773,404 B2 | 8/2004 | Poezevera et al. | |
| 6,786,866 B2 | 9/2004 | Odagiri et al. | |
| 6,799,072 B2 | 9/2004 | Ries et al. | |
| 6,810,287 B2 | 10/2004 | Zhu et al. | |
| 6,811,538 B2 | 11/2004 | Westbrook et al. | |
| 6,830,548 B2 | 12/2004 | Bonnet et al. | |
| 6,850,801 B2 | 2/2005 | Kieval et al. | |
| 6,857,428 B2 | 2/2005 | Thornton | |
| 6,890,306 B2 | 5/2005 | Poezevera | |
| 6,892,095 B2 | 5/2005 | Salo | |
| 6,904,320 B2 | 6/2005 | Park et al. | |
| 6,910,481 B2 | 6/2005 | Kimmel et al. | |
| 6,912,419 B2 | 6/2005 | Hill et al. | |

| | | |
|---|---|---|
| 6,922,589 B2 | 7/2005 | Stahmann et al. |
| 6,928,324 B2 | 8/2005 | Park et al. |
| 6,934,583 B2 | 8/2005 | Weinberg et al. |
| 6,959,214 B2 | 10/2005 | Pape et al. |
| 6,964,641 B2 | 11/2005 | Cho et al. |
| 6,988,498 B2 | 1/2006 | Berthon-Jones et al. |
| 6,999,817 B2 | 2/2006 | Park et al. |
| 7,025,729 B2 | 4/2006 | de Chazal et al. |
| 7,025,730 B2 | 4/2006 | Cho et al. |
| 7,027,871 B2 | 4/2006 | Burnes et al. |
| 7,039,468 B2 | 5/2006 | Freed et al. |
| 7,062,308 B1 | 6/2006 | Jackson |
| 7,081,095 B2 | 7/2006 | Lynn et al. |
| 7,089,936 B2 | 8/2006 | Madaus et al. |
| 7,092,755 B2 | 8/2006 | Florio |
| 7,094,207 B1 | 8/2006 | Koh |
| 7,110,820 B2 | 9/2006 | Tcheng et al. |
| 7,115,097 B2 | 10/2006 | Johnson |
| 7,117,036 B2 | 10/2006 | Florio |
| 7,127,290 B2 | 10/2006 | Girouard et al. |
| 7,130,687 B2 | 10/2006 | Cho et al. |
| 7,136,704 B2 | 11/2006 | Schulman |
| 7,149,574 B2 | 12/2006 | Yun et al. |
| 7,179,229 B1 | 2/2007 | Koh |
| 7,184,817 B2 | 2/2007 | Zhu et al. |
| 7,189,204 B2 | 3/2007 | Ni et al. |
| 7,194,313 B2 | 3/2007 | Libbus |
| 7,204,805 B2 | 4/2007 | Dean |
| 7,207,945 B2 | 4/2007 | Bardy |
| 7,212,862 B2 | 5/2007 | Park et al |
| 7,218,964 B2 | 5/2007 | Hill et al. |
| 7,225,013 B2 | 5/2007 | Geva et al. |
| 7,225,021 B1 | 5/2007 | Park et al. |
| 7,225,809 B1 | 6/2007 | Bowen et al. |
| 7,231,250 B2 | 6/2007 | Band et al. |
| 7,252,640 B2 | 8/2007 | Ni et al. |
| 7,269,459 B1 | 9/2007 | Koh |
| 7,277,757 B2 | 10/2007 | Casavant et al. |
| 7,289,854 B2 | 10/2007 | Bardy et al. |
| 7,292,890 B2 | 11/2007 | Whitehurst |
| 7,302,295 B2 | 11/2007 | Stahmann et al. |
| 7,308,311 B2 | 12/2007 | Sorensen et al. |
| 7,395,115 B2 | 7/2008 | Poezevera |
| 7,428,468 B2 | 9/2008 | Takemura et al. |
| 7,460,906 B2 | 12/2008 | Libbus |
| 7,481,759 B2 | 1/2009 | Whitehurst et al. |
| 7,486,991 B2 | 2/2009 | Libbus et al. |
| 7,509,166 B2 | 3/2009 | Libbus |
| 7,570,997 B2 | 8/2009 | Lovett et al. |
| 7,662,101 B2 | 2/2010 | Lee et al. |
| 7,747,323 B2 | 6/2010 | Libbus et al. |
| 2001/0000346 A1 | 4/2001 | Ruton et al. |
| 2001/0018547 A1 | 8/2001 | Mechlenburg et al. |
| 2002/0002327 A1 | 1/2002 | Grant et al. |
| 2002/0026221 A1 | 2/2002 | Hill et al. |
| 2002/0026222 A1 | 2/2002 | Schauerte et al. |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035379 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0049476 A1 | 4/2002 | Bardy et al. |
| 2002/0052636 A1 | 5/2002 | Bardy et al. |
| 2002/0058877 A1 | 5/2002 | Baumann et al. |
| 2002/0068958 A1 | 6/2002 | Bardy et al. |
| 2002/0072773 A1 | 6/2002 | Bardy et al. |
| 2002/0072776 A1 | 6/2002 | Osorio et al. |
| 2002/0082652 A1 | 6/2002 | Wentkowski et al. |
| 2002/0082658 A1 | 6/2002 | Heinrich et al. |
| 2002/0085741 A1 | 7/2002 | Shimizu |
| 2002/0091414 A1 | 7/2002 | Bardy et al. |
| 2002/0095184 A1 | 7/2002 | Bardy et al. |
| 2002/0103510 A1 | 8/2002 | Bardy et al. |
| 2002/0107544 A1 | 8/2002 | Ostroff et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107553 A1 | 8/2002 | Hill et al. |
| 2002/0107559 A1 | 8/2002 | Sanders et al. |
| 2002/0120299 A1 | 8/2002 | Ostroff et al. |
| 2002/0120304 A1 | 8/2002 | Mest |
| 2002/0136328 A1 | 9/2002 | Shimizu |
| 2002/0138563 A1 | 9/2002 | Trivedi |
| 2002/0143264 A1 | 10/2002 | Ding et al. |
| 2002/0143369 A1 | 10/2002 | Hill et al. |
| 2002/0161410 A1 | 10/2002 | Kramer et al. |
| 2002/0165586 A1 | 11/2002 | Hill et al. |
| 2002/0169384 A1 | 11/2002 | Kowallik et al. |
| 2002/0169485 A1 | 11/2002 | Pless et al. |
| 2002/0183237 A1 | 12/2002 | Puskas |
| 2002/0193685 A1 | 12/2002 | Mate et al. |
| 2002/0198570 A1 | 12/2002 | Puskas |
| 2003/0003052 A1 | 1/2003 | Hampton |
| 2003/0004546 A1 | 1/2003 | Casey |
| 2003/0004549 A1 | 1/2003 | Hill et al. |
| 2003/0004552 A1 | 1/2003 | Plombon et al. |
| 2003/0023175 A1 | 1/2003 | Arzbaecher et al. |
| 2003/0023279 A1 | 1/2003 | Spinelli et al. |
| 2003/0036773 A1 | 2/2003 | Whitehurst et al. |
| 2003/0036778 A1 | 2/2003 | Ostroff et al. |
| 2003/0045904 A1 | 3/2003 | Bardy et al. |
| 2003/0045909 A1 | 3/2003 | Gross et al. |
| 2003/0045914 A1 | 3/2003 | Cohen et al. |
| 2003/0050538 A1 | 3/2003 | Naghavi et al. |
| 2003/0055348 A1 | 3/2003 | Chazal et al. |
| 2003/0060857 A1 | 3/2003 | Perrson et al. |
| 2003/0060858 A1 | 3/2003 | Kieval et al. |
| 2003/0069609 A1 | 4/2003 | Thompson |
| 2003/0073919 A1 | 4/2003 | Hampton et al. |
| 2003/0074039 A1 | 4/2003 | Puskas |
| 2003/0078623 A1 | 4/2003 | Weinberg et al. |
| 2003/0078629 A1 | 4/2003 | Chen |
| 2003/0083241 A1 | 5/2003 | Young |
| 2003/0083587 A1 | 5/2003 | Ferek-Petric |
| 2003/0088027 A1 | 5/2003 | Chin et al. |
| 2003/0088278 A1 | 5/2003 | Bardy et al. |
| 2003/0088279 A1 | 5/2003 | Rissmann et al. |
| 2003/0088280 A1 | 5/2003 | Ostroff |
| 2003/0088281 A1 | 5/2003 | Ostroff et al. |
| 2003/0088282 A1 | 5/2003 | Ostroff |
| 2003/0088283 A1 | 5/2003 | Ostroff |
| 2003/0088286 A1 | 5/2003 | Ostroff et al. |
| 2003/0097153 A1 | 5/2003 | Bardy et al. |
| 2003/0100924 A1 | 5/2003 | Foreman et al. |
| 2003/0105493 A1 | 6/2003 | Salo et al. |
| 2003/0105497 A1 | 6/2003 | Zhu et al. |
| 2003/0121519 A1 | 7/2003 | Estes et al. |
| 2003/0139780 A1 | 7/2003 | Markowitz et al. |
| 2003/0149450 A1 | 8/2003 | Mayberg |
| 2003/0149457 A1 | 8/2003 | Tcheng et al. |
| 2003/0171687 A1 | 9/2003 | Irie et al. |
| 2003/0178031 A1 | 9/2003 | Du Pen et al. |
| 2003/0181951 A1 | 9/2003 | Cates |
| 2003/0195578 A1 | 10/2003 | Perron et al. |
| 2003/0204146 A1 | 10/2003 | Carlson |
| 2003/0209246 A1 | 11/2003 | Schroeder et al. |
| 2003/0212436 A1 | 11/2003 | Brown |
| 2003/0212440 A1 | 11/2003 | Boveja |
| 2003/0216789 A1 | 11/2003 | Deem et al. |
| 2003/0216792 A1 | 11/2003 | Levin et al. |
| 2003/0236558 A1 | 12/2003 | Whitehurst |
| 2004/0010303 A1 | 1/2004 | Bolea |
| 2004/0019364 A1 | 1/2004 | Kieval et al. |
| 2004/0039605 A1 | 2/2004 | Bardy |
| 2004/0059240 A1 | 3/2004 | Cho et al. |
| 2004/0073093 A1 | 4/2004 | Hatlestad |
| 2004/0111021 A1 | 6/2004 | Olson |
| 2004/0111040 A1 | 6/2004 | Ni et al. |
| 2004/0111041 A1 | 6/2004 | Ni et al. |
| 2004/0116981 A1 | 6/2004 | Mazar |
| 2004/0122487 A1 | 6/2004 | Hatlestad et al. |

| | | |
|---|---|---|
| 2004/0122488 A1 | 6/2004 | Mazar et al. |
| 2004/0128161 A1 | 7/2004 | Mazar et al. |
| 2004/0133079 A1 | 7/2004 | Mazar et al. |
| 2004/0134496 A1 | 7/2004 | Cho et al. |
| 2004/0163648 A1 | 8/2004 | Burton |
| 2004/0172074 A1 | 9/2004 | Yoshihito |
| 2004/0176695 A1 | 9/2004 | Poezevara |
| 2004/0176809 A1 | 9/2004 | Cho et al. |
| 2004/0193231 A1 | 9/2004 | David et al. |
| 2004/0199210 A1 | 10/2004 | Shelchuk |
| 2004/0210154 A1 | 10/2004 | Kline |
| 2004/0210261 A1 | 10/2004 | King et al. |
| 2004/0215240 A1 | 10/2004 | Lovett et al. |
| 2004/0215289 A1 | 10/2004 | Fukui |
| 2004/0230229 A1 | 11/2004 | Lovett et al. |
| 2004/0230230 A1 | 11/2004 | Lindstrom |
| 2004/0230243 A1 | 11/2004 | Haefner |
| 2004/0243012 A1 | 12/2004 | Ciaccio et al. |
| 2004/0254616 A1 | 12/2004 | Rossing et al. |
| 2005/0004615 A1 | 1/2005 | Sanders |
| 2005/0039745 A1 | 2/2005 | Stahmann et al. |
| 2005/0042589 A1 | 2/2005 | Hatlestad et al. |
| 2005/0043644 A1 | 2/2005 | Stahmann et al. |
| 2005/0043652 A1 | 2/2005 | Lovett et al. |
| 2005/0043772 A1 | 2/2005 | Stahmann et al. |
| 2005/0061315 A1 | 3/2005 | Lee et al. |
| 2005/0061319 A1 | 3/2005 | Hartley et al. |
| 2005/0065447 A1 | 3/2005 | Lee et al. |
| 2005/0065572 A1 | 3/2005 | Hartley et al. |
| 2005/0065575 A1 | 3/2005 | Dobak |
| 2005/0069322 A1 | 3/2005 | Tegge, Jr. et al. |
| 2005/0085864 A1 | 4/2005 | Schulman et al. |
| 2005/0085865 A1 | 4/2005 | Tehrani |
| 2005/0096705 A1 | 5/2005 | Pastore et al. |
| 2005/0101841 A9 | 5/2005 | Kaylor et al. |
| 2005/0107838 A1 | 5/2005 | Lovett et al. |
| 2005/0113710 A1 | 5/2005 | Stahmann et al. |
| 2005/0119711 A1 | 6/2005 | Cho et al. |
| 2005/0131467 A1 | 6/2005 | Boveja |
| 2005/0137645 A1 | 6/2005 | Voipio et al. |
| 2005/0142070 A1 | 6/2005 | Hartley et al. |
| 2005/0143779 A1 | 6/2005 | Libbus |
| 2005/0143785 A1 | 6/2005 | Libbus |
| 2005/0143787 A1 | 6/2005 | Boveja et al. |
| 2005/0145246 A1 | 7/2005 | Hartley et al. |
| 2005/0149126 A1 | 7/2005 | Libbus |
| 2005/0149127 A1 | 7/2005 | Libbus |
| 2005/0149128 A1 | 7/2005 | Heil, Jr. et al. |
| 2005/0149129 A1 | 7/2005 | Libbus et al. |
| 2005/0149131 A1 | 7/2005 | Libbus et al. |
| 2005/0149132 A1 | 7/2005 | Libbus |
| 2005/0149133 A1 | 7/2005 | Libbus et al. |
| 2005/0149143 A1 | 7/2005 | Libbus |
| 2005/0149155 A1 | 7/2005 | Scheiner et al. |
| 2005/0149156 A1 | 7/2005 | Libbus et al. |
| 2005/0159784 A1 | 7/2005 | Arceta |
| 2005/0165323 A1 | 7/2005 | Montgomery et al. |
| 2005/0197675 A1 | 9/2005 | David et al. |
| 2005/0240240 A1 | 10/2005 | Park et al. |
| 2006/0047333 A1 | 3/2006 | Tockmann et al. |
| 2006/0079945 A1 | 4/2006 | Libbus |
| 2006/0106428 A1 | 5/2006 | Libbus et al. |
| 2006/0106429 A1 | 5/2006 | Libbus et al. |
| 2006/0116737 A1 | 6/2006 | Libbus |
| 2006/0122675 A1 | 6/2006 | Libbus et al. |
| 2006/0206153 A1 | 9/2006 | Libbus et al. |
| 2006/0206154 A1 | 9/2006 | Libbus et al. |
| 2006/0217772 A1 | 9/2006 | Libbus et al. |
| 2006/0224188 A1 | 10/2006 | Libbus et al. |
| 2006/0293714 A1 | 12/2006 | Salo et al. |
| 2007/0005114 A1 | 1/2007 | Salo et al. |
| 2007/0093875 A1 | 4/2007 | Chavan et al. |
| 2007/0112388 A1 | 5/2007 | Salo |
| 2007/0142741 A1 | 6/2007 | Berthon-Jones et al. |
| 2007/0142871 A1 | 6/2007 | Libbus et al. |
| 2007/0150014 A1 | 6/2007 | Kramer et al. |
| 2007/0161873 A1 | 7/2007 | Ni et al. |
| 2007/0239057 A1 | 10/2007 | Pu et al. |
| 2007/0282215 A1 | 12/2007 | Ni et al. |

FOREIGN PATENT DOCUMENTS

| | | |
|---|---|---|
| EP | 0750920 | 1/1997 |
| EP | 0770407 | 5/1997 |
| EP | 1038498 | 9/2000 |
| EP | 1162125 | 12/2001 |
| EP | 1 172 125 A1 | 1/2002 |
| EP | 1234597 | 8/2002 |
| EP | 1304137 | 4/2003 |
| EP | 1317943 | 6/2003 |
| EP | 1486232 | 12/2004 |
| EP | 1541193 | 6/2005 |
| WO | WO8402080 | 6/1984 |
| WO | WO8605965 | 10/1986 |
| WO | WO9203983 | 3/1992 |
| WO | WO9217240 | 10/1992 |
| WO | WO9220402 | 11/1992 |
| WO | WO9301862 | 2/1993 |
| WO | WO9904841 | 2/1999 |
| WO | WO0009206 | 2/2000 |
| WO | WO0017615 | 3/2000 |
| WO | WO0124876 | 4/2001 |
| WO | WO0143804 | 6/2001 |
| WO | WO0176689 | 10/2001 |
| WO | WO0226318 | 4/2002 |
| WO | WO0234327 | 5/2002 |
| WO | WO02085448 | 10/2002 |
| WO | WO03003905 | 1/2003 |
| WO | WO03011388 | 2/2003 |
| WO | WO03041559 | 5/2003 |
| WO | WO03075744 | 9/2003 |
| WO | WO03076008 | 9/2003 |
| WO | WO03082080 | 10/2003 |
| WO | WO03099373 | 12/2003 |
| WO | WO03099377 | 12/2003 |
| WO | WO2004012814 | 2/2004 |
| WO | WO2004062485 | 7/2004 |
| WO | WO2004084990 | 10/2004 |
| WO | WO2004084993 | 10/2004 |
| WO | WO2004103455 | 12/2004 |
| WO | WO2004105870 | 12/2004 |
| WO | WO2004110549 | 12/2004 |
| WO | WO2005018739 | 3/2005 |
| WO | WO2005028029 | 3/2005 |
| WO | WO2005042091 | 5/2005 |
| WO | WO2005053788 | 6/2005 |
| WO | WO2005063332 | 7/2005 |
| WO | WO2005065771 | 7/2005 |
| WO | WO2006031331 | 3/2006 |

OTHER PUBLICATIONS

Stephane Garrigue, MD, Philippe Bordier, MD, Meleze Hocini, MD, Pierre Jaïs, MD, Michel Haïssaguerre, MD and Jacques Clementy, MD, "Night Atrial Overdrive with DDD Pacing: A New Therapy for Sleep Apnea Syndrome", Hopital Cardiologique du Haut-Leveque, University of Bordeaux, Pessac-Bordeaux, France, p. 591.

Terry Young, Ph.D., Mari Palta, Ph.D., Jerome Dempsey, Ph.D., James Skatrud, MD, Steven Weber, Ph.D., and Safwan Badr, MD. "The Occurrence of Sleep-disordered Breathing Among Middle-aged Adults", The New England Journal of Medicine, vol. 328, No. 17, pp. 1230-1235.

T. Douglas Bradley, MD and John S. Floras, MD,DPhIL, "Pathophysiologic and Therapeutic Implications of Sleep Apnea in Congestive Heart Failure", Toronto, Ontario, Canada, Journal of Cardiac Failure, vol. 2, No. 3, pp. 223-240.

Stephane Garrigue, Philippe Bordier, Meleze Hocini, Pierre Jais, Michel Haissaguerre and Jacques Clementy, Night Atrial Overdrive with DDD Pacing Results in a Significant Reduction of Sleep Apnea Episodes and QOL Improvement in Heart Failure Patients, Hosp. Cardiologique du Haut-Leveque, Bordeaux-Pessac, France, Abstract Session 25, p. 145.

Krzysztof W. Balaban, Yong Cho, Luc Mongeon, Lynn Liu, Nancy Foldvary, Richard Burgess, Christoph Scharf, Reto Candinas and Bruce L. Wilkoff, "Feasibility of Screening for Sleep Apnea using Pacemaker Impedance Sensor", Cleveland Clin. Fdn, Cleveland, OH, Medtronic, Inc., Minneapolis, MN, Strong Memorial Hosp., Rochester, NY and Univ. Hosp., Zurich, Switzerland, p. 313.

S. Javaheri, MD, T.J.Parker, MD, J.D. Liming, MD, W.S. Corbett, BS, H. Nishiyama, MD, L. Wexler, MD and G.A. Roselle, MD, "Sleep Apnea in 81 Ambulatory Male Patients with Stable Heart Failure", from the Sleep Disorders Laboratory, Department of Veterans Affairs Medical Center, and the Department of Medicine, University of Cincinnati College of Medicine, Cincinnati, OH, pp. 2154-2159.

Aircraft Noise and Sleep Disturbance: Final Report', prepared by the Civil Aviation Authority London on behalf of the Department of Trade, Aug. 1980 (CAA Report).

Altshule et al., The Effect of Position on Periodic Breathing in Chronic Cardiac Decomposition, New Eng. Journal of Med., vol. 259, No. 22, pp. 1064-1066, Nov. 27, 1958.

Andersen, Long-term follow-up of patients from a randomized trial of atrial versus ventricular pacing for sick-sinus syndrome, Lancet, 350(9086), Oct. 25, 1997, 1210-6. Abstract only.

Benchimol, Cardiac hemodynamics during stimulation of the right atrium, right ventricle, and left ventricle in normal and abnormal hearts, Circulation, 33(6), Jun. 1966, 933-44.

Bevan et al., Postganglionic sympathetic delay in vascular smooth muscle, Journal of Pharmacology & Experimental Therapeutics, 152(2), May 1966, 211-30.

Bevan et al., Sympathetic nerve-free vascular muscle, Journal of Pharmacology & Experimental Therapeutics, 157(1), Jul. 1967, 117-24.

Bilgutay et al. A new concept in the treatment of hypertension utilizing an implantable electronical device: Baropacer. Trans. Am. Society Artificial Internal Organs. 1964. vol. 10, pp. 387-395.

Bilgutay et al., Vagal tuning for the control of supraventricular arrhythmias, Surgical Forum, 16, 1965, 151-3.

Borst et al., Optimal frequency of carotid sinus nerve stimulation in treatment of angina pectoris, Cardiovascular Research, 8(5), Sep. 1974, 674-80.

Bradley et al, Cardiac Output Response to Continuous Positive Airway Pressure in Congestive Heart Failure, 145 Am. Rev. Respir. Dis. 377-382, 1992.

Bradley et al., Sleep Apnea and Heart Failure, Park I: Obstructive Sleep Apnea, 107 Circulation 1671-1678, 2003.

Braunwald et al., Carotid sinus nerve stimulation in the treatment of angina pectoris and supraventricular trachycardia, California Medicine, 112(3), Mar. 1970, 41-50.

Braunwald et al., Relief of angina pectoris by electrical stimulation of the carotid-sinus nerves, New England Journal of Medicine, 277(24), Dec. 14, 1967, 1278-83.

Buda et al., Effect of Intrathoracic Pressure on Left Ventricular Performance, 301 Engl. J. Med. 453-459, 1979, Abstract only.

Calvin et al., Positive End-Expiratory Pressure (PEEP) Does Not Depress Left Ventricular Function in Patients With Pulmonary Edema, 124 Am. Rev. Respir. Dis. 121-128, 1981, Abstract only.

Chapleau, Contrasting effects of static and pulsatile pressure on carotid baroreceptor activity in dogs, Circulation, vol. 61, No. 5, Nov. 1987, pp. 648-658.

Chapleau, Pulsatile activation of baroreceptors causes central facilitation of baroreflex, American Journal Physiol Heart Circ Physiol, Jun. 1989, 256:H1735-1741.

Coleridge et al. "The distribution, connexions and histology of baroreceptors in the pulmonary artery, with some observations on the sensory innervation of the ductus arteriosus." Physiology, May 1961, pp. 591-602.

Cooper et al., Neural effects on sinus rate and atrioventricular conduction produced by electrical stimulation from a transvenous electrode catheter in the canine right pulmonary artery, Circulation Research, 46(1), Jan. 1980, 48-57.

Dart Jr. et al., Carotid sinus nerve stimulation treatment of angina refractory to other surgical procedures, Annals of Thoracic Surgery, 11(4), Apr. 1971, 348-59.

De Hoyos et al., Haemodynamic Effects of Continuous Positive Airway Pressure in Humans With Normal and Impaired Left Ventricular Function, 88 Clin. Sci., Lond. 173-8, 1995, Abstract only.

De Landsheere et al., Effect of spinal cord stimulation on regional myocardial perfusion assessed by positron emission tomography, American Journal of Cardiology, 69(14), May 1, 1992, 1143-9, Abstract only.

Dunning, Electrostimulation of the Carotid Sinus Nerve in Angina Pectoris, University Department of Medicine, Binnengasthuis, Amsterdam: Printed by Royal VanGorcum, Assen, Netherlands, 1971, 1-92.

Epstein et al., Treatment of angina pectoris by electrical stimulation of the carotid-sinus nerves, New England Journal of Medicine, 280(18), May 1, 1969, 971-8.

Farrehi, Stimulation of the carotid sinus nerve in treatment of angina pectoris, American Heart Journal, 80(6), Dec. 1970, 759-65.

Feliciano et al., Vagal nerve stimulation releases vasoactive intestinal peptide which significantly increases coronary artery blood flow, Cardiovascular Research, 40(1), Oct. 1998, 45-55.

Fromer et al., Ultrarapid subthreshold stimulation for termination of atrioventricular node reentrant tachycardia, Journal of the American College of Cardiology, 20(4), Oct. 1992, 879-83, Abstract only.

Gallois et al., Multi-Channel Analysis of the EEG Signals and Statistic Particularities for Epileptic Seizure Forecast, Second Joint EMBS/BMES Conference, pp. 208-215, Oct. 23-26, 2002.

Giardino et al., Respiratory Sinus Arrhythmia is Associated with the Efficiency of Pulmonary Gas Exchange in Healthy Humans, 284 Am. J. Physiol. H1585-1591, 2003. Abstract only.

Gradaus et al., Nonthoracotomy Implantable Cardioverter Defibrillator Placement in Children: Use of a Subcutaneous Array Leads and Abdominally Placed Implantable Cardioverter Defibrillators in Children, J. of Cardiovascular Electrophysiology, vol. 12, No. 3, pp. 356-360, Mar. 2001.

Grassi et al., Baroreflex and non-baroreflex modulation of vagal cardiac control after myocardial infarction, Am J Cardiol, 84(5), Sep. 1, 1999, 525-9, Abstract only.

Griffith et al., Electrical Stimulation of the Carotid Sinus Nerve in Normotensive and Renal Hypertensive Dogs, Circulation, 28, Jul.-Dec. 1963, 730.

Hanson et al., Cardiac Gated Ventilation, 2433 SPIE 303-308, 1995.

Hartz et al., New Approach to Defibrillator Insertion, J. Thoracic Cardiovascular Surgery, vol. 97, pp. 920-922, 1989.

Henning, Effects of autonomic nerve stimulation, asynchrony, and load on dP/dtmax and on dP/dtmin, American Journal of Physiology, 260(4PT2), Apr. 1991, H1290-8.

Henning et al., Vagal nerve stimulation increases right ventricular contraction and relaxation and heart rate, Cardiovascular Research, 32(5), Nov. 1996, 846-53.

Hilton et al., Evaluation of Frequency and Time-frequency Spectral Analysis of Heart Rate Variability as a Diagnostic Marker of the Sleep Apnea Syndrome. Med Biol Eng Comput Nov. 1999, 37(6), 760-9. Abstract only.

Hood Jr. et al., Asynchronous contraction due to late systolic bulging at left ventricular pacing sites, American Journal of Physiology, 217(1), Jul. 1969, 215-21.

Ishise, Time course of sympathovagal imbalance and left ventricular dysfunction in conscious dogs with heart failure, Journal of Applied Physiology 84(4), Apr. 1998, 1234-41.

Janes, "Anatomy of human extrinsic cardiac nerves and ganglia", Am J Cardiol., 57(4), Feb. 1, 1986, 299-309.

Javaheri et al., Sleep Apnea in 81 Ambulatory Male Patients with Stable Heart Failure, from the Sleep Disorders Laboratory, Department of Veterans Affairs Medical Center, and the Department of Medicine, University of Cincinnati College of Medicine, Cincinnati, OH, pp. 2154-2159.

Jessurun et al., Coronary blood flow dynamics during transcutaneous electrical nerve stimulation for stable angina pectoris associated with severe narrowing of one major coronary artery, American Journal of Cardiology, 82(8), erratum appears in Am J Cardiol, Feb. 1999, 15;83(4):642, Oct. 15, 1998, 921-6.

Junyu et al., Posture Detection Algorithm Using Multi Axis DC-Accelerometer, Pace vol. 22, Apr. 1999.

Kandel et al., Part VII: Arousal, Emotion, and Behavioral Homeostasis, In: Principles of neural science, New YorK:McGraw-Hill, Health Professions Division, 2000, 966-969.

Karpawich et al., Altered cardiac histology following apical right ventricular pacing in patients with congenital atrioventricular block, Pacing Clin Electrophysiol, 22(9), Sep. 1999, 1372-7, Abstract only.

Kaye et al., Acute Effects of Continuous Positive Airway Pressure on Cardiac Sympathetic Tone in Congestive Heart Failure, 103 Circulation 2336-24338, 2001.

Kolettis et al., Submammary Implantation of a Cardioverter-Defibrillator with a Nonthoractomy Lead System, Am. Heart J., vol. 126, pp. 1222-1223, Nov. 1993.

Krahn et al. Recurrent syncope. Experience with an implantable loop record. Cardiol. Clin., vol. 15(2), May 1997, pp. 316-326 Abstract only.

Laude et al., Effects of Breathing Pattern on Blood Pressure and Heart Rate Oscillations in Humans, 20 Clin. Exp. Pharmol. Phisiol 619, 625, 1993. Abstract only.

Leclercq et al., Hemodynamic importance of preserving the normal sequence of ventricular activation in permanent cardiac pacing, Am Heart J., 129(6), Jun. 1995, 1133-41, Abstract only.

Lenique et al., Ventilatory and Hemodynamic Effects of Continuous Positive Airway Pressure in Left Heart Failure, 155 Am. J. Respir. Crit. Care Med. 500-505, 1997. Abstract only.

Li, "Vagal nerve stimulation markedly improves long-term survival after chronic heart failure in rats", Circulation, 109(1), Epub Dec. 8, 2003, Jan. 6, 2004, 1-5.

Lugaresi et al., Snoring, 39 Electroencephalogr. Clin. Neurophysiol. 59-64, 1975.

Mannheimer et al., Epidural spinal electrical stimulation in severe angina pectoris, British Heart Journal, 59(1), Jan. 1988, 56-61, Abstract only.

Mannheimer et al., Transcutaneous electrical nerve stimulation in severe angina pectoris, European Heart Journal, 3(4), Aug. 1982, 297-302, Abstract only.

Mannheimer et al., Transcutaneous electrical nerve stimulation (TENS) in angina pectoris, Pain, 26(3), Sep. 1986, 291-300, Abstract only.

Mansfield, D. et al., Effects of Continuous Positive Airway Pressure on Lung Function in Patients with Chronic Obstructive Pulmonary Disease and Sleep Disordered Breathing, Respirology 365-70, 1999. Abstract only.

Mazgalev et al., Autonomic modification of the atrioventricular node during atrial fibrillation: role in the slowing of ventricular rate, Circulation 99(21), Jun. 1, 1999, 2806-14.

Mehta et al., Effects of Continuous Positive Airway Pressure on Cardiac Volumes In Patients With Ischemic and Dilated Cardiomyopathy, 161 Am. J. Respir. Crit. Care Med. 128-134, 2000.

Millar-Craig et al., Circadian variation of blood-pressure, Lancet, 1(8068), Apr. 15, 1978, 795-7, Abstract only.

Minisi et al., Regional left ventricular deafferentation increases baroreflex sensitivity following myocardial infarction, Cardiovasc Res., 58(1), Apr. 1, 2003, 136-41, Abstract only.

Murphy et al., Intractable angina pectoris: management with dorsal column stimulation, Medical Journal of Australia, 146(5), Mar. 2, 1987, 260, Abstract only.

Naughton et al., Effects of Continuous Positive Airway Pressure on Intrathoracic and Left Ventricular Transmural Pressure in Congestive Heart Failure, 91 Circulation 1725-1731, 1995, pp. 1-25.

Neil et al. "Effects of electrical stimulation of the aortic nerve on blood pressure and respiration in cats and rabbits under chloralose and nembutal anaesthesia." *Journal of Physiology*. Sep. 1949. vol. 109 (3-4), pp. 392-401.

Neistadt et al., Effects of electrical stimulation of the carotid sinus nerve in reversal of experimentally induced hypertension, Surgery, 61(6), Jun. 1967, 923-31.

Park et al., Use of an Implantable Cardioverter Defibrillator in an Eight-Month-Old Infant with Ventricular Fibrillation Arising from a Myocardial Fibroma, PACE, vol. 22, No. 1, pp. 138-139, Jan. 1999.

Peters et al. "Tempral and spatial summation caused by aortic nerve stimulation in rabbits. Effects of stimulation frequencies and amplitudes." Journal of the Autonomic Nervous System. 1989. vol. 27, pp. 193-205, Abstract only.

Peters et al., The principle of electrical carotid sinus nerve stimulation: a nerve pacemaker system for angina pectoris and hypertension therapy, Annals of Biomedical Engineering, 8(4-6), 1980, 445-58, Abstract only.

Philbin et al., Inappropriate shocks delivered by an ICD as a result of sensed potentials from a transcutaneous electronic nerve stimulation unit, Pacing & Clinical Electrophysiology, 21(10), Oct. 1998, 2010-1, Abstract only.

Pinsky et al., Hemodynamic Effect of Cardiac Cycle-Specific Increases in Intrathoracic Pressure, 6 J. Appl. Physiol. 604-612 ,1986. Abstract only.

Potkin et al., Effect of positive end-expiratory pressure on right and left ventricular function in patients with the adult respiratory distress syndrome, 135 Am. Rev. Respir. Dis. 307-311, 1987. Abstract only.

Prakash et al. Asymmetrical distribution of aortic nerve fibers in the pig, Anat Rec., 158(1), May 1967, 51-7, Abstract only.

Reddel et al., Analysis of Adherence to Peak Flow Monitoring When Recording of Data is Electronic, BMJ 146-147, 2002.

Rees et al., Paroxysmal Nocturnal Dyspnoea and Periodic Respiration, The Lancet, Dec. 22-29, 1979, pp. 1315-1317, Abstract only.

Rosenqvist, The effect of ventricular activation sequence on cardiac performance during pacing, Pacing and Electrophysiology, 19(9), 1996, 1279-1286.

Rushmer, Chapter 5—Systemic Arterial Pressure, In: Cardiovascular dynamics, Philadelphia: Saunders, 1976, 176-216.

Sato et al. "Novel Therapeutic Strategy against Central Baroreflex Failure: A Bionic Baroreflex System." Circulation. Jul. 1999, vol. 100, pp. 299-304.

Satoh et al., "Role of Hypoxic Drive in Regulation of Postapneic Ventilation During Sleep in Patients with Obstructive Sleep Apnea", Am Rev Respir Dis, Mar. 1991 143 (3): 481-485.

Scharf, Effects of Continuous Positive Airway Pressure on Cardiac Output in Experimental Heart Failure, 19 Sleep S240-2, 1996. Abstract only.

Schauerte et al., Catheter stimulation of cardiac parasympathetic nerves in humans: a novel approach to the cardiac autonomic nervous system, Circulation, 104(20), Nov. 13, 2001, 2430-5.

Schauerte et al., Transvenous parasympathetic cardiac nerve stimulation: an approach for stable sinus rate control, Journal of Cardiovascular Electrophysiology, 10(11), Nov. 1999, 1517-24.

Schauerte, Transvenous Parasympathetic Nerve Stimulation in the Inferior Vena Cava and Atrioventricular Conduction, Journal of Cardiovascular Electrophysiology, 11(1), Jan. 2000, 64-69.

Schauerte et al., Ventricular rate control during atrial fibrillation by cardiac parasympathetic nerve stimulation: a transvenous approach, Journal of the American College of Cariology, 34(7), Dec. 1999, 2043-50.

Scherlag, Endovascular Neural Stimulation via a Novel Basket Electrode Catheter: Comparison of Electrode Configurations, Journal of Interventional Cardiac Electrophysiology, 4(1), Apr. 2000, 219-224, Abstract only.

Schuder et al., Experimental Ventricular Defibrillation with an Automatic and Completely Implanted System, Trans. Am. Soc. Artif. Int. Organs, vol. 16, pp. 207-212, 1970.

Schuder et al., Ventricular Defibrillation in the Dog Using Implanted and Partially Implanted Electrode Systems, Am. J. of Cardiology, vol. 33, pp. 243-247, Feb. 1974.

Schuder et al., Transthoracic Ventricular Defibrillation in the Dog with Truncated and Untruncated Exponential Stimuli, IEEE Trans. On Bio-Medical Engin., vol. BME-18, No. 6, pp. 410-415, Nov. 1971.

Smits et al., Defibrillation Threshold (DFT) Model of a Fully Subcutaneous ICD System, Europace Supplements, vol. 2, Jun. 2001 at col. 778, p. B83.

Stirbis et al., Optmizing the Shape of Implanted Artificial Pacemakers, Kaunas Medical Institute. Translated from Meditsinskaya Tekhnika, No. 6, pp. 25-27, 1986.

Takahashi, Vagal modulation of ventricular tachyarrhythmias induced by left ansae subclaviae stimulation in rabbits, Japanese Heart Journal, 39(4), Jul. 1998, 503-11, Abstract only.

Thrasher et al., Unloading arterial baroreceptors causes neurogenic hypertension, American Journal Physiol. Regulatory Integrative Comp. Physiol. 2002. vol. 282, R1044-R1053.

Tkacova et al., Left Ventricular Volume in Patients with Heart Failure and Cheyne-Strokes Respiration during Sleep, Am. Journal, Respir. Crit. Care Med., vol. 156, pp. 1549-1555, 1997.

Tse et al., Long-term effect of right ventricular pacing on myocardial perfusion and function, J Am Coll Cardiol., 29(4), Mar. 15, 1997, 744-9.

Vanoli, Vagal stimulation and prevention of sudden death in conscious dogs with a healed myocardial infarction, Circulation Research, 68(5), May 1991, 1471-81, Abstract only.

Veerman et al., Circadian profile of systemic hemodynamics, Hypertension, 26(1), Jul. 1995, 55-9.

Verity et al., Pulmonary artery innvervation: a morphopharmacologic correlation, Proceedings of the Western Pharmacology Society, 8, 1965, 57-9.

Verity et al., Plurivesicular nerve endings in the pulmonary artery, Nature, 211(48), Jul. 30, 1966, 537-8, Abstract only.

Wallick, Selective AV nodal vagal stimulation improves hemodynamics during acute atrial fibrillation in dogs, American Journal of Physiology—Heart & Circulatory Physiology, 281(4), Oct. 2001, H1490-7.

Waninger et al., Electrophysiological control of ventricular rate during atrial fibrillation, Pacing & Clinical Electrophysiology, 23(8), Aug. 2000, 1239-44, Abstract only.

Weber et al., Effects of CPAP and BIPAP on stroke volume in patients with obstructive sleep apnea syndrome. Pneumolgie Mar. 1995; 49(3):233-5. Translated Abstract only.

Wiggers et al., The muscular reactions of the mammalian ventricles to artificial surface stimuli, American Journal of Physiology, 1925, 346-378.

Young et al., The Occurrence of Sleep-disordered Breathing Among Middle-aged Adults, The New England Journal of Medicine, vol. 328, No. 17, pp. 1230-1235.

Zarzoso et al., Noninvasive Fetal Electrocardiogram Extraction: Blind Separation Versus Adaptive Noise Cancellation, IEEE Transactions on Biomedical Engineering, vol. 48, No. 1, pp. 12-18, Jan. 2001.

Zhang et al., Optimal ventricular rate slowing during atrial fibrillation by feedback AV nodal-selective vagal stimulation, American Journal of Physiology—Heart & Circulatory Physiology, 282(3), Mar. 2002, H1102-10.

Zhou et al., Prevention of high incidence of neurally mediated ventricular arrhythmias by afferent nerve stimulation in dogs, Circulation, 101(7), Feb. 22, 2000, 819-24.

Office Action dated Jun. 29, 2007 from co-pending U.S. Appl. No. 10/643,016, filed Aug. 18, 2003.

File History for U.S. Appl. No. 10/939,834 as retrieved from U.S. Patent and Trademark Office on Feb. 13, 2011, 405 pages.

File History for U.S. Appl. No. 10/939,711 as retrieved from U.S. Patent and Trademark Office on Feb. 13, 2011, 367 pages.

Ajilore et al., Nightcap: Laboratory and home-based evaluation of a portable sleep monitor, 32 Psychophysiology, 32-98, 1995. Abstract only.

Baratz et al., Effect of Nasal Continuous Positive Airway Pressure on Cardiac Output and Oxygen Delivery in Patients With Congestive Heart Failure, 102 Chest, 1992, 397-401.

Garrigue et al., Benefit of Atrial Pacing in Sleep Apnea Syndrome, 346 N. Engl. J. Med. 404-412, 2002.

Hoffman et al., Cheyne-Stokes Respiration in Patients Recovering from Acute Cardiogenic Pulmonary Edema, Chest 1990, 97:410-12.

Javaheri, A Mechanism of Central Sleep Apnea in Patients With Heart Failure, 341 N. Engl. J. Med. 949-954, 1999.

Javaheri et al., Sleep Apnea in 81 Ambulatory Male Patients with Stable Heart Failure: Types and Their Prevalences, Consequences, and Presentations, 97 Circulation 2154-2159, 1998.

Leng et al., Lead Configuration for Defibrillator Implantation in a Patient with Congenital Heart Disease and a Mechanical Prosthetic Tricuspid Valve, PACE, vol. 24, pp. 1291-1292, Aug. 2001.

Pinsky et al., Augmentation of Cardiac Function by Elevation of Intrathoracic Pressure, 54 J. Appl. Physiol., 1983, 950-955.

Rasanen et al., Acute Myocardial Infarction Complicated by Left Ventricular Dysfunction and Respiratory Failure. The Effects of Continuous Positive Airway Pressure, 87 Chest, 1985, 158-62.

Roche et al., Screening of Obstructive Sleep Apnea Syndrome by Heart Rate Variability Analysis, 100 Circulation 1411-1455, 1999.

Steltner et al., Diagnosis of Sleep Apnea by Automatic Analysis of Nasal Pressure and Forced Oscillation Impedance. Am. Journal Respiratory Critical Care Medicine, vol. 165, pp. 940-944, 2002.

Stirbis et al., Optimizing the Shape of Implanted Artificial Pacemakers, Kaunas Medical Institute. Translated from Meditsinskaya Tekhnika, No. 6, pp. 25-27, 1986.

Vanninen et al., Cardiac Sympathovagal Balance During Sleep Apnea Episodes, 16 Clin. Physiol. 209-216, 1996.

Waldemark et al., Detection of Apnea using Short Window FFT Technique and Artificial Neural Network, 3390 SPIE International Society for Optical Engineering 122-133, 1998.

Office Action from U.S. Appl. No. 10/643,203 dated Mar. 31, 2008, 6 pages.

Office Action Response dated Jun. 19, 2008 to office action dated Mar. 31, 2008 from U.S. Appl. No. 10/643,203, 7 pages.

Office Action from U.S. Appl. No. 10/643,203 dated Sep. 22, 2008, 17 pages.

Office Action Response dated Dec. 22, 2008 to office action dated Sep. 22, 2008 from U.S. Appl. No. 10/643,203, 12 pages.

Office Action from U.S. Appl. No. 10/643,203 dated Apr. 29, 2009, 8 pages.

Office Action Response dated Jul. 23, 2009 to office action dated Apr. 29, 2009 from U.S. Appl. No. 10/643,203, 10 pages.

Notice of allowance for U.S. Appl. No. 10/643,203 dated Dec. 17, 2009, 4 pages.

Office Action from U.S. Appl. No. 10/939,639 dated Oct. 16, 2006, 17 pages.

Office Action Response submitted Feb. 16, 2007 to office action dated Oct. 16, 2006 for U.S. Appl. No. 10/939,639, 15 pages.

Office Action from U.S. Appl. No. 10/939,639 dated Jun. 5, 2007, 13 pages.

Office Action Response submitted Aug. 6, 2007 to office action dated Jun. 5, 2007 for U.S. Appl. No. 10/939,639, 8 pages.

Office Action from U.S. Appl. No. 10/939,639 dated Oct. 2, 2007, 7 pages.

Office Action Response submitted Feb. 4, 2008 to office action dated Oct. 2, 2007 for U.S. Appl. No. 10/939,639, 9 pages.

Office Action from U.S. Appl. No. 10/939,639 dated May 13, 2008, 8 pages.

Office Action Response submitted Aug. 8, 2008 to office action dated May 13, 2008 for U.S. Appl. No. 10/939,639, 9 pages.

Office Action from U.S. Appl. No. 10/939,639 dated Nov. 18, 2008, 10 pages.

Office Action Response submitted Feb. 10, 2009 to office action dated Nov. 18, 2008 for U.S. Appl. No. 10/939,639, 10 pages.

Office Action Response submitted Apr. 20, 2009 to office action dated Nov. 18, 2008 for U.S. Appl. No. 10/939,639, 9 pages.

Notice of Allowance for U.S. Appl. No. 10/939,639 dated Jun. 30, 2009, 4 pages.

Office Action from European patent application No. 04784602.7 dated May 9, 2007, 3 pages.

Office Action Response to European patent application No. 04784602.7 dated Jan. 10, 2008, 3 pages.

Office Action Response to European patent application No. 04784602.7, dated Apr. 17, 2008, 9 pages.

PCT/US2004/030787 International Search Report dated Sep. 29, 2005, 12 pages.

* cited by examiner

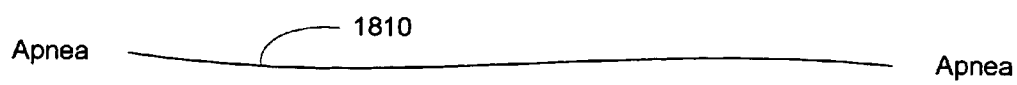

SLEEP QUALITY DATA COLLECTION AND EVALUATION

FIELD OF THE INVENTION

The present invention relates generally to collecting and evaluating information related to sleep quality.

BACKGROUND OF THE INVENTION

Sleep is generally beneficial and restorative to a patient, exerting great influence on the quality of life. The human sleep/wake cycle generally conforms to a circadian rhythm that is regulated by a biological clock. Regular periods of sleep enable the body and mind to rejuvenate and rebuild. The body may perform various tasks during sleep, such as organizing long term memory, integrating new information, and renewing tissue and other body structures.

Normal sleep is characterized by a general decrease in metabolic rate, body temperature, blood pressure, breathing rate, heart rate, cardiac output, sympathetic nervous activity, and other physiological functions. However, studies have shown that the brain's activity does not decrease significantly during sleep. Normally a patient alternates between rapid eye movement (REM) and non-REM (NREM) sleep in approximately 90 minute cycles throughout a sleep period. A typical eight hour sleep period may be characterized in terms of a five-step sleep cycle identifiable through EEG brain wave activity.

Non-REM sleep includes four sleep states or stages that range from light dozing to deep sleep. Throughout NREM sleep, muscle activity is still functional, breathing is low, and brain activity is minimal. Approximately 85% of the sleep cycle is spent in NREM sleep. Stage 1 NREM sleep may be considered a transition stage between wakefulness and sleep. As sleep progresses to stage 2 NREM sleep, eye movements become less frequent and brain waves increase in amplitude and decrease in frequency. As sleep becomes progressively deeper, the patient becomes more difficult to arouse. Stage 3 sleep is characterized by 20 to 40% slow brain wave (delta) sleep as detected by an electroencephalogram (EEG). Sleep stages 3 and 4 are considered to be the most restful sleep stages.

REM sleep is associated with more prevalent dreaming, rapid eye movements, muscle paralysis, and irregular breathing, body temperature, heart rate and blood pressure. Brain wave activity during REM sleep is similar to brain wave activity during a state of wakefulness. There are typically 4-6 REM periods per night, with increasing duration and intensity toward morning. While dreams can occur during either REM or NREM sleep, the nature of the dreams varies depending on the type of sleep. REM sleep dreams tend to be more vivid and emotionally intense than NREM sleep dreams. Furthermore, autonomic nervous system activity is dramatically altered when REM sleep is initiated.

Lack of sleep and/or decreased sleep quality may be have a number of causal factors including, e.g., nerve or muscle disorders, respiratory disturbances, and emotional conditions, such as depression and anxiety. Chronic, long-term sleep-related disorders e.g., chronic insomnia, sleep-disordered breathing, and sleep movement disorders, including restless leg syndrome (RLS), periodic limb movement disorder (PLMD) and bruxism, may significantly affect a patient's sleep quality and quality of life.

Movement disorders such as restless leg syndrome (RLS), and a related condition, denoted periodic limb movement disorder (PLMD), are emerging as one of the more common sleep disorders, especially among older patients. Restless leg syndrome is a disorder causing unpleasant crawling, prickling, or tingling sensations in the legs and feet and an urge to move them for relief. RLS leads to constant leg movement during the day and insomnia or fragmented sleep at night. Severe RLS is most common in elderly people, although symptoms may develop at any age. In some cases, it may be linked to other conditions such as anemia, pregnancy, or diabetes.

Many RLS patients also have periodic limb movement disorder (PLMD), a disorder that causes repetitive jerking movements of the limbs, especially the legs. These movements occur approximately every 20 to 40 seconds and cause repeated arousals and severely fragmented sleep.

A significant percentage of patients between 30 and 60 years experience some symptoms of disordered breathing, primarily during periods of sleep. Sleep disordered breathing is associated with excessive daytime sleepiness, systemic hypertension, increased risk of stroke, angina and myocardial infarction. Disturbed respiration can be particularly serious for patients concurrently suffering from cardiovascular deficiencies. Disordered breathing is particularly prevalent among congestive heart failure patients, and may contribute to the progression of heart failure.

Sleep apnea is a fairly common breathing disorder characterized by periods of interrupted breathing experienced during sleep. Sleep apnea is typically classified based on its etiology. One type of sleep apnea, denoted obstructive sleep apnea, occurs when the patient's airway is obstructed by the collapse of soft tissue in the rear of the throat. Central sleep apnea is caused by a derangement of the central nervous system control of respiration. The patient ceases to breathe when control signals from the brain to the respiratory muscles are absent or interrupted. Mixed apnea is a combination of the central and obstructive apnea types. Regardless of the type of apnea, people experiencing an apnea event stop breathing for a period of time. The cessation of breathing may occur repeatedly during sleep, sometimes hundreds of times a night and occasionally for a minute or longer.

In addition to apnea, other types of disordered respiration have been identified, including, for example, hypopnea (shallow breathing), dyspnea (labored breathing), hyperpnea (deep breathing), and tachypnea (rapid breathing).

Combinations of the disordered respiratory events described above have also been observed. For example, Cheyne-Stokes respiration (CSR) is associated with rhythmic increases and decreases in tidal volume caused by alternating periods of hyperpnea followed by apnea and/or hypopnea. The breathing interruptions of CSR may be associated with central apnea, or may be obstructive in nature. CSR is frequently observed in patients with congestive heart failure (CHF) and is associated with an increased risk of accelerated CHF progression.

An adequate duration and quality of sleep is required to maintain physiological homeostasis. Untreated, sleep disturbances may have a number of adverse health and quality of life consequences ranging from high blood pressure and other cardiovascular disorders to cognitive impairment, headaches, degradation of social and work-related activities, and increased risk of automobile and other accidents.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

SUMMARY OF THE INVENTION

Various embodiments of present invention involve methods and systems for collecting sleep quality data and evaluating the sleep quality of a patient.

An embodiment of the invention involves a method for collecting sleep quality data. The method includes detecting physiological and non-physiological conditions associated with the sleep quality of a patient and collecting sleep quality data based on the detected conditions. Collecting the sleep quality data is performed at least in part implantably.

Another embodiment of the invention involves a method for evaluating sleep quality. In accordance with this method, one or more metrics associated with sleep are determined. One or more metrics associated with events that disrupt sleep are determined. A composite sleep quality metric is determined using the one or more metrics associated with sleep and the one or more metrics associated with events that disrupt sleep.

In yet another embodiment of the invention, a method for evaluating sleep quality includes detecting physiological and non-physiological conditions associated with the sleep quality of a patient and collecting sleep quality data based on the detected conditions. The sleep quality of the patient is evaluated using the collected data. At least one of collecting the sleep quality data and evaluating the sleep quality of the patient is performed at least in part implantably.

Another embodiment of the invention involves a method for evaluating sleep quality. One or more conditions associated with sleep quality of a patient are detected during a period of wakefulness. Sleep quality data is collected based on the detected conditions. The patient's sleep quality is evaluated using the collected sleep quality data. At least one of collecting the data and evaluating the sleep quality is performed at least in part implantably.

A further embodiment of the invention involves a medical device including a detector system configured to detect physiological and non-physiological conditions associated with sleep quality and a data collection system for collecting sleep quality data based on the detected conditions. The data collection system includes an implantable component.

Yet another embodiment of the invention relates to a medical device configured to evaluate sleep quality. The medical device includes a detector system configured to detect physiological and non-physiological conditions associated with the sleep quality of a patient. A sleep quality processor, coupled to the detection system, is configured to determine metrics based on the detected conditions. The metrics include one or more metrics associated with sleep, one or more metrics associated with events that disrupt sleep, and at least one composite sleep quality metric based on the one or more metrics associated with sleep and the one or more metrics associated with events that disrupt sleep.

In another embodiment of the invention, a medical device for assessing sleep quality includes a detector unit configured to detect physiological and non-physiological conditions associated with sleep quality and a sleep quality data collection unit configured to collect sleep quality data based on the detected conditions. A data analysis unit coupled to the data collection unit evaluates sleep quality based on the collected sleep quality data. At least one of the data collection unit and the data analysis unit includes an implantable component.

A further embodiment of the invention involves a system for collecting sleep quality data. The system includes means for detecting physiological and non-physiological conditions associated with sleep quality and means for collecting sleep quality data based on the detected conditions. The means for collecting the sleep quality data includes an implantable component.

In yet another embodiment of the invention, a system for assessing sleep quality includes means for determining one or more metrics associated with sleep and means for determining one or more metrics associated with events that disrupt sleep. The system further includes means for determining a composite sleep quality metric as a function of the metrics associated with sleep and the metrics associated with events that disrupt sleep.

Another embodiment of the invention involves a system for evaluating sleep quality. The system includes means for detecting physiological and non-physiological conditions associated with sleep quality and means for collecting sleep quality data based on the detected conditions. The system includes means for evaluating the sleep quality of the patient based on the collected sleep quality data. At least one of the means for collecting the sleep quality data and the means for evaluating the sleep quality comprise an implantable component.

A further embodiment involves a system for evaluating the sleep quality of a patient. The system includes means for detecting one or more patient conditions associated with sleep quality during a period of wakefulness and means for collecting sleep quality data based on the detected conditions. The system further includes means for evaluating the sleep quality of the patient using the collected sleep quality data. At least one of the means for collecting the sleep quality data and means for evaluating the sleep quality include an implantable component.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIGS. 18C-G are graphs illustrating disordered breathing events comprising a combination of apnea and hypopnea respiration cycles;

Figure 1:
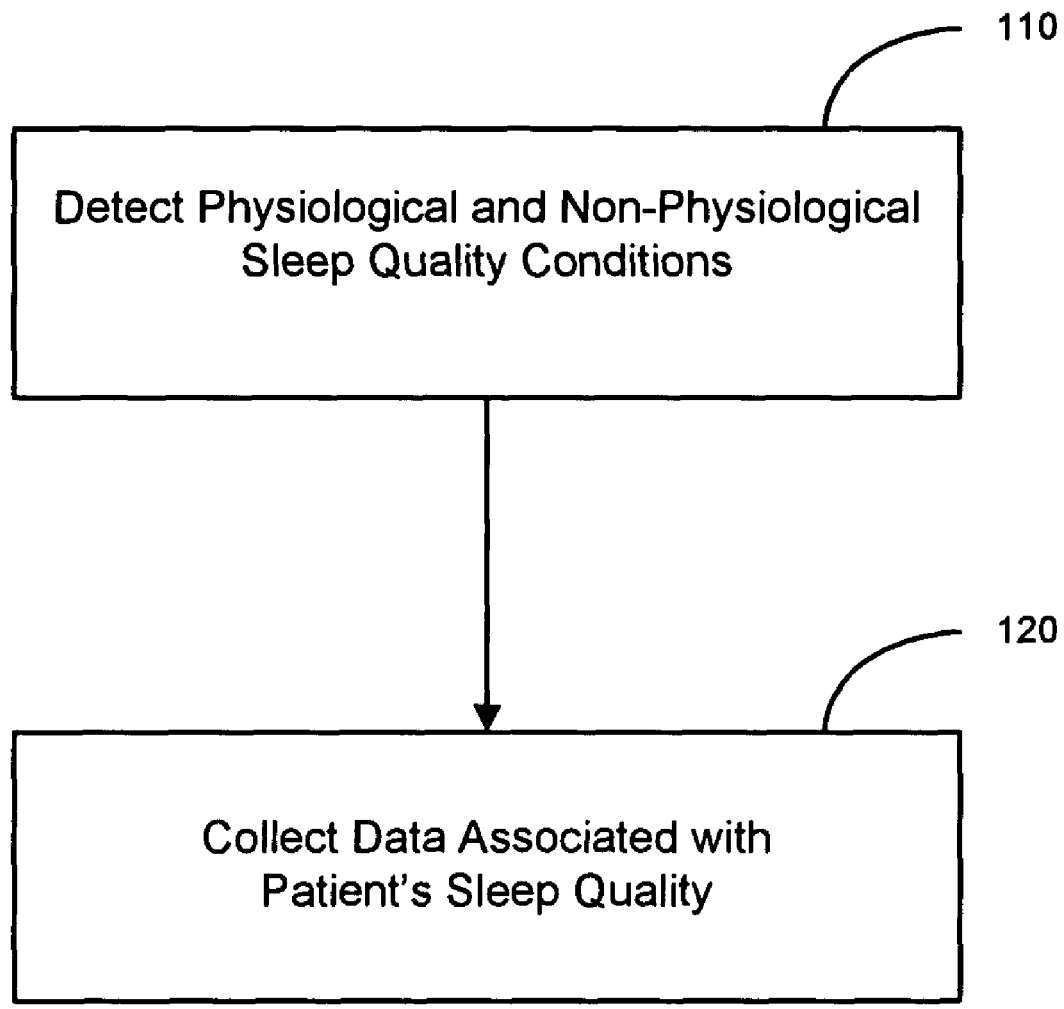
FIG. 1 is a flow chart illustrating a method of collecting sleep quality data in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which are shown, by way of illustration, various embodiments by which the invention may be practiced. It is to be understood that other embodiments may be utilized. Structural and functional changes may be made without departing from the scope of the present invention.

Sleep quality assessments depend upon acquiring sleep-related data, including the patient's typical sleep patterns and the physiological, environmental, contextual, emotional, and other conditions affecting the patient during sleep. Diagnosis of sleep disorders and assessment of sleep quality often involves the use of a polysomnographic sleep study at a dedicated sleep facility. However, such studies are costly, inconvenient to the patient, and may not accurately represent the patient's typical sleep behavior. In a polysomnographic sleep study, the patient is instrumented for data acquisition and observed by trained personnel. Sleep assessment in a laboratory setting presents a number of obstacles in acquiring an accurate picture of a patient's typical sleep patterns. For example, spending a night in a sleep laboratory typically causes a patient to experience a condition known as "first night syndrome," involving disrupted sleep during the first few nights in an unfamiliar location. In addition, sleeping while instrumented and observed may not result in a realistic perspective of the patient's normal sleep patterns.

Further, polysomnographic sleep studies provide an incomplete data set for the analysis of some sleep disorders, including, for example, sleep disordered breathing. A number of physiological conditions associated with sleep disordered breathing are detectable during periods of wakefulness, e.g., decreased heart rate variability, elevated sympathetic nerve activity, norepinephrine concentration, and increased blood pressure variability. Collection of data during periods of sleep and/or during periods of wakefulness may provide a more complete picture of the patient's sleep quality.

Various aspects of sleep quality, including number and severity of arousals, sleep disordered breathing episodes, nocturnal limb movements, and cardiac, respiratory, muscle, and nervous system functioning may provide important information for diagnosis and/or therapy delivery. An initial step to sleep quality evaluation is an accurate and reliable method for discriminating between periods of sleep and periods of wakefulness. Further, acquiring data regarding the patient's sleep states or stages, including sleep onset, termination, REM, and NREM sleep states may be used in connection sleep quality assessment. For example, the most restful sleep occurs during stages 3 and 4 NREM sleep. One indicator of sleep quality is the percentage of time a patient spends in these sleep stages. Knowledge of the patient's sleep patterns may be used to diagnose sleep disorders and/or adjust patient therapy, including, e.g., cardiac or respiratory therapy. Trending disordered breathing episodes, arousal episodes, and other sleep quality aspects may be helpful in determining and maintaining appropriate therapies for patients suffering from disorders ranging from snoring to chronic heart failure.

The present invention involves methods and systems for acquiring sleep quality data using one or more implantable components. As illustrated in FIG. 1, methods of the invention involve detecting conditions associated with the sleep quality of the patient 110, including physiological and non-physiological conditions. Data related to the patient's sleep quality is collected based on the detected conditions 120. Detection of patient conditions related to sleep quality may occur during periods of wakefulness and/or during periods of sleep. Either detecting the conditions associated with sleep quality, or collecting the sleep quality data, or both, is performed using a device having a component that is at least in part implantable.

A representative set of the conditions associated with sleep quality is listed in Table 1. Patient conditions used to evaluate sleep quality may include, for example, both physiological and non-physiological (i.e., contextual) conditions. Physiological conditions associated with sleep quality may be further organized, for example, into conditions of the cardiovascular, respiratory, muscle, and nervous systems, and conditions relating to the patient's blood chemistry.

Contextual conditions may be further subdivided into environmental conditions, body-related conditions and historical/background conditions. Environmental conditions may be broadly defined to include the environmental surroundings affecting the patient, such as ambient light, temperature, humidity, air pollution, noise, and barometric pressure. Body-related conditions may include, for example, patient location, posture, and altitude. Contextual conditions relevant to sleep quality may also include historical or background conditions. For example, a patient's medical/psychological history, gender, age, weight, body mass index, neck size, drug use, and emotional state may be detected and used in connection with sleep quality evaluation and sleep disorder diagnosis. Methods and systems for detecting contextual conditions are described in commonly owned U.S. Pat. No. 7,400,928, which is incorporated herein by reference.

TABLE 1

| Condition Type | | Condition | Sensor type or Detection method |
|---|---|---|---|
| Physiological | Cardiovascular System | Heart rate | EGM, ECG |
| | | Heart rate variability | |
| | | QT interval | |
| | | Ventricular filling pressure | Intracardiac pressure sensor |
| | | Blood pressure | Blood pressure sensor |
| | Respiratory System | Snoring | Accelerometer |
| | | | Microphone |
| | | Respiration pattern (Tidal volume Minute ventilation Respiratory rate) | Transthoracic impedance sensor (AC) |
| | | Patency of upper airway | Intrathoracic impedance sensor |
| | | Pulmonary congestion | Transthoracic impedance sensor (DC) |
| | Nervous System | Sympathetic nerve activity | Muscle sympathetic nerve Activity sensor |
| | | Brain activity | EEG |
| | Blood Chemistry | CO2 saturation | Blood analysis |
| | | O2 saturation | |
| | | Blood alcohol content | |
| | | Adrenalin | |
| | | Brain Natriuretic Peptide (BNP) | |
| | | C-Reactive Protein | |
| | | Drug/Medication/Tobacco use | |
| | Muscle System | Muscle atonia | EMG |
| | | Eye movement | EOG |
| | | Patient activity | Accelerometer, MV, etc. |
| | | Limb movements | Accelerometer |
| | | Jaw movements | |
| Non-physiological | Environmental | Ambient temperature | Thermometer |
| | | Humidity | Hygrometer |
| | | Pollution | Air quality website |
| | | Time | Clock |
| | | Barometric pressure | Barometer |
| | | Ambient noise | Microphone |
| | | Ambient light | Photodetector |
| | Body-related | Posture | Posture sensor |
| | | Altitude | Altimeter |
| | | Location | GPS, proximity sensor |
| | | Proximity to bed | Proximity to bed sensor |
| | Historical/ Background | Historical sleep time | Patient input, previously detected sleep onset times |
| | | Medical history | Patient input device |
| | | Age | |
| | | Recent exercise | |
| | | Weight | |
| | | Gender | |
| | | Body mass index | |
| | | Neck size | |
| | | Emotional state | |
| | | Psychological history | |
| | | Daytime sleepiness | |
| | | Patient perception of sleep quality | |
| | | Drug, alcohol, nicotine use | |

Each of the conditions listed in Table 1 may serve a variety of purposes in evaluating sleep quality. For example, a subset of the conditions may be used to detect whether the patient is asleep and to track the various stages of sleep and arousal incidents. Another subset of the conditions may be used to detect disordered breathing episodes. Yet another subset may be used to detect abnormal limb movements. In one implementation, some or all of the listed conditions may be collected over a relatively long period of time and used to analyze long term sleep quality trends. Trending may be used in connection with an overall assessment of sleep quality and diagnosis and treatment of sleep-disordered breathing, movement disorders, and/or other sleep disorders.

In one implementation, sleep quality analysis may be used within the structure of an advanced patient management system. In this implementation, an advanced patient management system having sleep quality analysis capability allows a physician to remotely and automatically monitor cardiac and respiratory functions, as well as other patient conditions, including information related to sleep quality. In one example, an implantable cardiac rhythm management system, such as a cardiac monitor, pacemaker, defibrillator, or resynchronization device, may be equipped with various telecommunications and information technologies to enable real-time data collection, diagnosis, and treatment of the patient. Systems and methods involving advanced patient management techniques are described in U.S. Pat. Nos. 6,336,903, 6,312,378, 6,270,457, and 6,398,728 which are incorporated herein by reference in their respective entireties.

Table 2 provides examples of how some physiological and non-physiological conditions may be used in connection with sleep quality assessment.

TABLE 2

| Condition Type | Condition | Examples of how condition is used in sleep quality assessment |
| --- | --- | --- |
| Physiological | Heart rate | Decrease in heart rate may indicate disordered breathing episode. |
| | | Decrease in heart rate may indicate the patient is asleep. |
| | Heart rate variability | May be used to determine sleep state. |
| | | Changes in heart rate variability, detected during periods of sleep or wakefulness, may indicate that the patient suffers from sleep disordered breathing. |
| | QT interval | May be used to detect sleep apnea. |
| | Ventricular filling pressure | May be used to identify/predict pulmonary congestion associated with respiratory disturbance. |
| | Blood pressure | Variation in blood pressure is associated with apnea. |
| | Snoring | Associated with a higher incidence of obstructive sleep apnea and may be used to detect disordered breathing. |
| | Respiration pattern | May be used to detect disordered breathing episodes. |
| | | May be used to determine the type of disordered breathing. |
| | | May be used to detect sleep. |
| | Patency of upper airway | Related to obstructive sleep apnea and may be used to detect episodes of obstructive sleep apnea. |
| | Pulmonary congestion | Associated with respiratory disturbances. |
| | Sympathetic nerve activity (SNA) | Apnea termination is associated with a spike in SNA. |
| | | SNA activity may be elevated during periods of wakefulness if the patient experiences sleep disordered breathing. |
| | Electroencephalogram (EEG) | May be used to determine sleep stages, including REM and NREM sleep stages |
| | CO2 saturation | Low CO2 levels may indicate initiation of central apnea. |
| | O2 saturation | O2 desaturation occurs during severe apnea/hypopnea episodes. |
| | Blood alcohol content | Alcohol tends to increase the incidence of snoring & obstructive apnea. |
| | Adrenalin | End of apnea associated with a spike in blood adrenaline. |
| | Brain Natriuretic Peptide (BNP) | A marker of heart failure status, which is associated with Cheyne-Stokes Respiration. |
| | C-Reactive Protein | A measure of inflammation that may be related to apnea. |
| | Drug/Medication/Tobacco use | These substances may affect incidence of both central & obstructive apnea. |
| | Muscle atonia | Muscle atonia may be used in connection with detection of REM and non-REM sleep. |
| | Eye movement | Eye movement may be used in connection with detection of REM and non-REM sleep. |
| | Activity | May be used to detect sleep and patient well being. |
| | Limb movements | May be used to detect abnormal limb movements during sleep. |
| Non-physiological | Ambient Temperature | Ambient temperature may predispose the patient to episodes of disordered breathing during sleep. |
| | Humidity | Humidity may predispose the patient to episodes of disordered breathing during sleep. |
| | Pollution | Pollution may predispose the patient to episodes of disordered breathing during sleep. |
| | Posture | Posture may be used to determine if the patient is asleep. |
| | | Posture may predispose the patient to disordered breathing. |
| | Time | Used to establish historical sleep time. |
| | Ambient noise level | Noise level may affect sleep quality. |
| | Location | Patient location may used to determine if the patient is in bed as a part of sleep detection. |
| | Altitude | Altitude may predispose the patient to episodes of disordered breathing and may affect sleep quality. |
| | Barometric Pressure | Barometric pressure may predispose the patient to episodes of disordered breathing. |
| | Proximity to bed | May be used to determine if patient is in bed. |
| | Historical sleep time | May be used in connection with sleep detection. |
| | Medical history | History of medical disorders, e.g., CHF, that are associated with disordered breathing such as Cheyne-Stokes respiration. |
| | Age | Age is associated with increased risk of disordered breathing, RLS and other sleep disruptive disorders. |
| | Weight | Associated with sleep disordered breathing, e.g., obstructive sleep apnea. |
| | Gender | |
| | Obesity | |
| | Neck size | |
| | Patient reported drug, alcohol, nicotine use | Patient drug, alcohol and nicotine use may affect sleep quality. |
| | Psychological history | Psychological factors, e.g., clinical depression may be associated with insomnia. |
| | Emotional state | Emotional state, e.g., stress, anxiety, euphoria, may affect sleep quality. |

TABLE 2-continued

| Condition Type | Condition | Examples of how condition is used in sleep quality assessment |
|---|---|---|
| | Daytime sleepiness Patient perceptions of sleep quality | May be used to evaluate sleep quality. |

Figure 2:
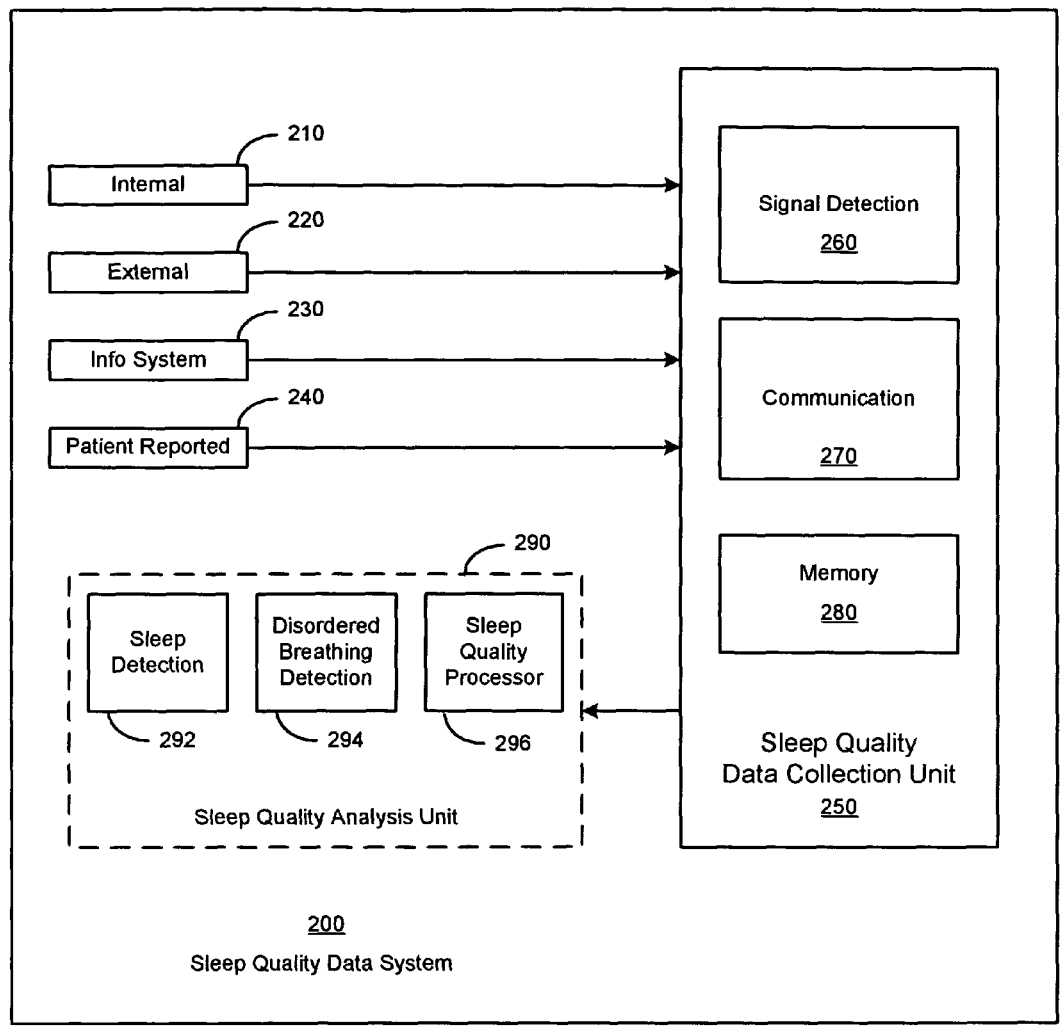
FIG. 2 illustrates a block diagram of a sleep quality data system in accordance with embodiments of the invention.

FIG. 2 illustrates a block diagram of a sleep quality data system 200 configured in accordance with embodiments of the invention. In this implementation, the sleep quality data system 200 may use signals acquired from a variety of sources to collect data relevant to sleep quality. The collected data may be stored in the memory 280 of a data collection unit 250 and/or transmitted to a sleep quality analysis unit 290 for further processing. It is contemplated that at least one, some, or all components of the system 200 are implanted in the patient.

The sleep quality data system 200 may use patient-internal sensors 210 implanted within the body of the patient to detect physiological conditions relevant to sleep quality. The conditions detected using patient-internal sensors 210 may include, for example, heart rate, respiratory pattern, and patient activity.

The system 200 may also use patient-external sensors 220 to detect physiological or non-physiological patient conditions. In one example configuration, whether the patient is snoring may be useful in evaluating sleep quality. Snoring data may be detected using an external microphone and transferred to the sleep quality data collection unit 250. In another configuration, ambient temperature and humidity may be factors related to the patient's sleep quality. The ambient temperature and humidity of the patient's room may be sensed using sensors located near patient. Signals from the temperature and humidity sensors may be transmitted to the data collection unit 250. Limb and/or jaw movements may be sensed using patient-external accelerometers and/or other sensors placed in appropriate locations on or near the patient and transmitted to the data collection unit 250.

Information relevant to sleep quality may also be reported 240 by the patient. According to embodiments of the invention, the patient's self-described conditions, including medication use, tobacco use, perceptions of sleep quality, and/or psychological or emotional state, for example, may be relevant to sleep quality assessment. The patient may enter information about these conditions through an appropriate interface device, such as a medical device programmer, coupled to the sleep quality data collection unit 250.

Some information related to sleep quality may be accessible through information systems 230, including network-based systems. For example, information about the patient's present cardiac, respiratory, or other therapy may be downloaded from an external device via a wireless or wired network. In another example, information about conditions affecting the patient, such as local air quality data, may be accessed through an internet-connected website.

The patient-internal sensors 210, patient-external sensors 220, patient-reported input devices 240, and information systems 230, may be coupled to the data collection unit 250 in a variety of ways. In one example, one or more of the sensors 210, 220, patient-reported input devices 240, and information systems 230 have wireless communication capabilities, such as a wireless Bluetooth communications link, or other proprietary communications protocol. In this implementation, the devices having wireless communication capabilities may remotely transmit signals to the data collection unit 250. In this application, the data collection unit 250 may be configured as an implantable or patient-external device. In other implementations, one or more of the patient-internal sensors 210, patient-external sensors 220, patient-reported input devices 240, and information systems 230 may be coupled to the data collection unit 250 through leads or other wired connections.

The implantable or patient-external data collection unit 250 includes detection circuitry 260 for processing signals from the sensors 210, 220, patient-reported input devices 240, and information systems 230. The detection circuitry 260 may include, for example, amplifiers, filters, A/D converters, signal processors and/or sensor driver circuitry configured to provide sensor signals used in the evaluation of sleep quality. The data collection unit 250 may further include wireless communication circuitry 270 for receiving and transmitting signals to wirelessly connected components.

In one embodiment, the sleep quality data system 200 collects data from the sensors 210, 220, input devices 240, and information systems 230, and stores the collected data in memory 280 prior to further processing or transmission. In another embodiment, the sleep quality data system 200 may transmit the collected data to a separate device (not shown) for storage, analysis, or display.

In a further embodiment, the sleep quality data system 200 may evaluate or further process the collected sleep quality data. For this purpose, the sleep quality data system 200 may optionally include a sleep quality analysis unit 290. In one configuration, the data collection unit 250 and the sleep quality analysis unit 290 are arranged in separate devices. In such a configuration, the data collection unit 250 transfers the collected sleep quality data to the sleep quality analysis unit 290 through a wireless or wired connection. In another configuration, the sleep quality analysis unit 290 and the data collection unit 250 are arranged within the same device which may be a patient-external device or a fully or partially implantable device.

The sleep quality analysis unit 290 may include one or more subsystems useful in sleep quality assessment. The subsystems may include, for example a sleep detector 292 used to detect sleep onset, sleep offset, and arousal, for example. The sleep detector may also detect sleep stages, including the various stages of NREM and REM sleep. The sleep quality analysis unit 290 may include circuitry to detect various sleep-related disorders. For example, the sleep quality analysis unit 290 may include circuitry 294 for detecting disordered breathing and circuitry 295 for detecting abnormal nocturnal movements. Further, the sleep quality analysis unit 290 may include a processor for evaluating sleep quality 296, for example, by calculating one or more metrics quantifying the patient's sleep quality.

Figure 3:
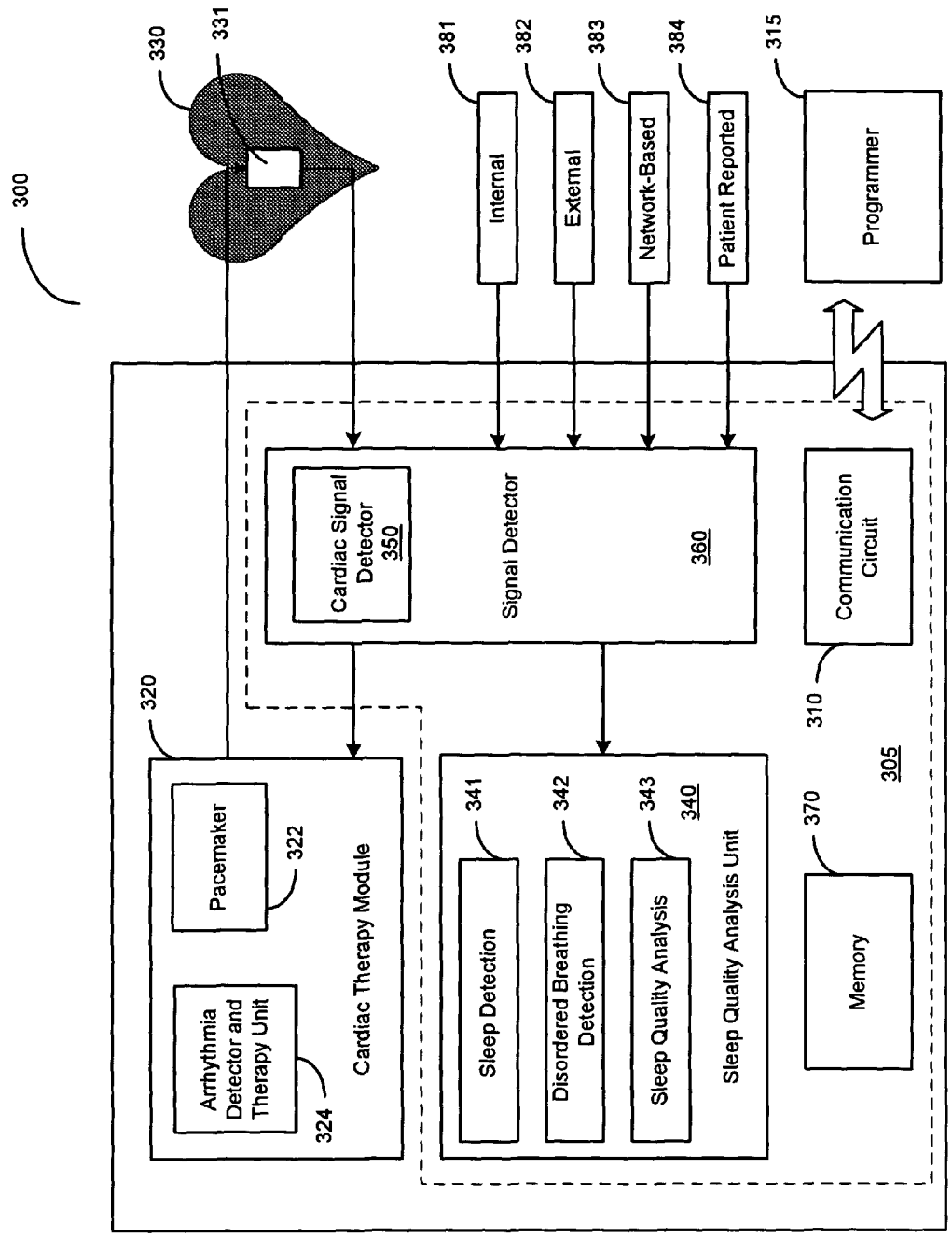
FIG. 3 is a system block diagram illustrating a sleep quality data system incorporated within a cardiac rhythm management system in accordance with embodiments of the invention.

FIG. 3 illustrates a sleep quality data system 305 incorporated within a cardiac rhythm management system (CRM) 300. The CRM 300 may include, for example, a cardiac therapy module 320 including a pacemaker 322 and an arrhythmia detector/therapy unit 324. The cardiac therapy module 320 is coupled to a lead system having electrodes 331 implantable within the patient's body. The implanted electrodes 331 are arranged to receive signals from the heart 330 and deliver stimulation therapy to the heart 330. Cardiac signals sensed using the implanted electrodes 331 are received by a cardiac signal detector 350 coupled to the cardiac therapy module 320.

The cardiac therapy module 320 analyzes the cardiac signals to determine an appropriate therapy to treat arrhythmia conditions affecting the heart 330. The cardiac therapy may include pacing therapy controlled by the pacemaker 322 to treat cardiac rhythms that are too slow. The pacemaker 322 controls the delivery of periodic low energy pacing pulses to ensure that the periodic contractions of the heart are maintained at a hemodynamically sufficient rate.

The cardiac therapy may also include therapy to terminate tachyarrhythmia, wherein the heart rate is too fast. The arrhythmia detector/therapy unit 324 analyzes cardiac signals received from the cardiac signal detector 350 to recognize tachyarrhythmias including atrial or ventricular tachycardia or fibrillation. The arrhythmia detector/therapy unit 324 recognizes cardiac signals indicative of tachyarrhythmia and delivers high energy stimulations to the heart 330 through the implanted electrodes 331 to terminate the arrhythmias.

Various input devices, including implantable sensors 381, patient-external sensors 382, patient input devices 384, and information systems 383 may be coupled to the CRM 300. These devices 381, 382, 383, 384 may be used to provide information about physiological and/or non-physiological conditions affecting the patient relevant to sleep quality, such as the representative set of patient conditions listed in Table 1 above.

The CRM 300 includes signal detection circuitry 360 for receiving and processing signals from the various sensors and input devices 381, 382, 384, 383. As previously discussed, the signal detection circuitry 360 may include signal processing circuitry configured to amplify, digitize, or otherwise process signals representing the sensed sleep quality conditions. In the illustrated implementation, the patient input devices 384, patient-external sensors 382, and information systems 383 are wirelessly coupled to the CRM 300. The patient-internal sensors 381 may be coupled to the CRM 300 through leads, through a wireless link, or integrated within or on the housing of the CRM 300 (e.g., integral accelerometer).

In one embodiment, the sleep quality data system 305 incorporated within the CRM 300 collects data from cardiac electrodes 331, patient-internal sensors 381, patient-external sensors 382, patient input devices 384, and information systems 383 and stores the collected data in memory. The sleep quality data system may transmit the collected data to a separate device, such as the CRM programmer 315 or other device, periodically as required or desired.

In another embodiment, the CRM sleep quality data system 305 may perform further processing and/or evaluation of the sleep quality data. For this purpose, the CRM sleep quality data system 305 may include a sleep quality analysis unit 340 coupled to the signal detector 360. The sleep quality analysis unit 340 may include one or more components for evaluating the patient's sleep quality. For example, the sleep quality analysis unit 340 may include sleep detection circuitry 341, disordered breathing detection circuitry 342, abnormal nocturnal movement detection circuitry 344, and a sleep quality processor 343, as previously described in connection with FIG. 2.

The cardiac therapy module 320, signal detector 360, and sleep quality analysis unit 340 operate in cooperation with a memory unit 370. The memory unit 370 may store parameters associated with cardiac therapy in addition to diagnostic or other data related to cardiac functioning and sleep quality. A communication unit 310 located within the CRM 300 may be used to transmit programming information and collected data from the CRM 300 to an external device such as a programmer 315.

Sleep quality assessment involves a reliable method for discriminating between a state of sleep and a state of wakefulness. One method of detecting sleep involves comparing one or more detected physiological conditions to thresholds indicative of sleep. When the detected conditions are consistent with thresholds indicating sleep, then sleep onset is declared. For example, decreased patient activity is a condition associated with sleep. When the patient's activity falls below a predetermined threshold, the system declares the onset of sleep. When the patient's activity rises above the threshold, the system declares the end of sleep. In a similar manner, a number of patient conditions, such as heart rate, respiration rate, brain wave activity, etc., may be compared individually or collectively compared to thresholds or other indices to detect sleep.

An enhanced method of sleep detection is described in commonly owned U.S. Pat. No. 7,189,204, which is incorporated herein by reference. The method involves adjusting a sleep threshold associated with a first patient condition using a second patient condition. The first patient condition is compared to the adjusted threshold to determine if the patient is asleep or awake.

Figure 4:
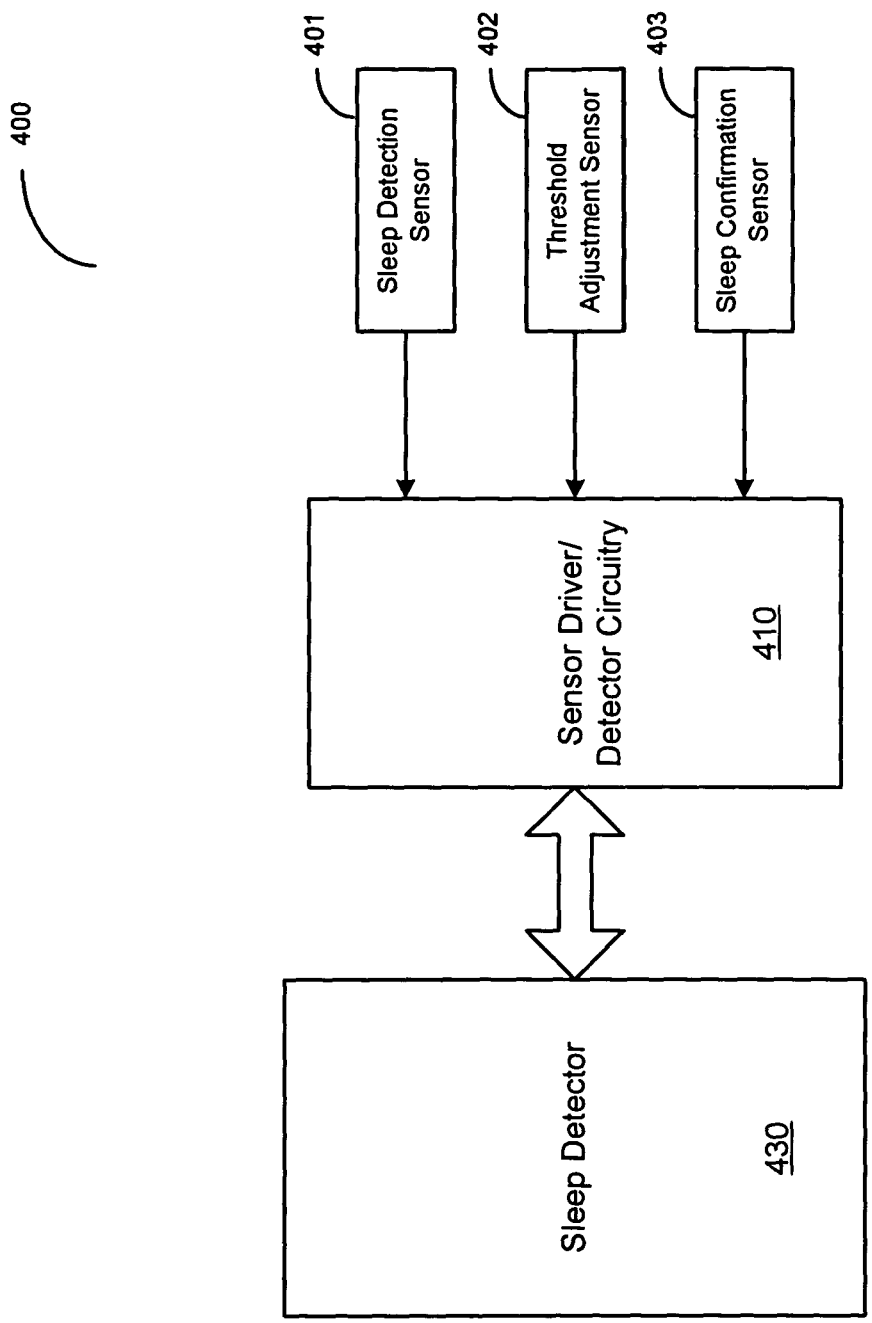
FIG. 4 is a block diagram of a sleep detection unit that may be used as part of a sleep quality data system according to embodiments of the invention.

FIG. 4 is a block diagram of a sleep detection unit 400 that may be used as part of a sleep quality data system according to embodiments of the invention. The sleep detection unit 400 uses a number of sensors 401, 402, 403 to sense sleep-related patient conditions. A representative set of sleep-related conditions include, for example, patient activity, patient location, posture, heart rate, QT interval, eye movement, respiration rate, transthoracic impedance, tidal volume, minute ventilation, brain activity, muscle tone, body temperature, time of day, and blood oxygen level.

According to embodiments of the invention, a first sleep-related condition detected using a sleep detection sensor 401 is compared to a sleep threshold for detecting the onset and termination of sleep. A second sleep-related condition, detected using a threshold adjustment sensor 402, is used to adjust the sleep threshold. Although the example described herein involves one sleep detection sensor 401 and one threshold adjustment sensor 402, any number of thresholds or other indices corresponding to a number of sleep detection sensors may be used. Furthermore, conditions detected using any number of adjustment sensors may be used to adjust the thresholds or indices of a plurality of sleep detection signals. Additional sleep-related signals derived from one or more confirmation sensors 403 may optionally be used to confirm the onset or termination of the sleep condition.

Signals derived from the sensors 401, 402, 403 are received by a sensor driver/detection circuitry 410 that may include, for example, amplifiers, signal processing circuitry, and/or A/D conversion circuitry for processing each sensor signal. The sensor driver/detection system 410 may further include sensor drive circuitry required to activate the sensors 401, 402, 403.

The sensor signal detection system 410 is coupled to a sleep detector 430. The sleep detector 430 is configured to compare the level of a first sleep-related condition detected using the sleep detection sensor 401 to a sleep threshold adjusted by a second sleep-related condition detected using the threshold adjustment sensor 402. A determination of sleep onset or sleep termination may be made by the sleep detector 430 based on the comparison. The onset or termination of sleep may optionally be confirmed using patient conditions derived using a sleep confirmation sensor 403.

Figure 5:
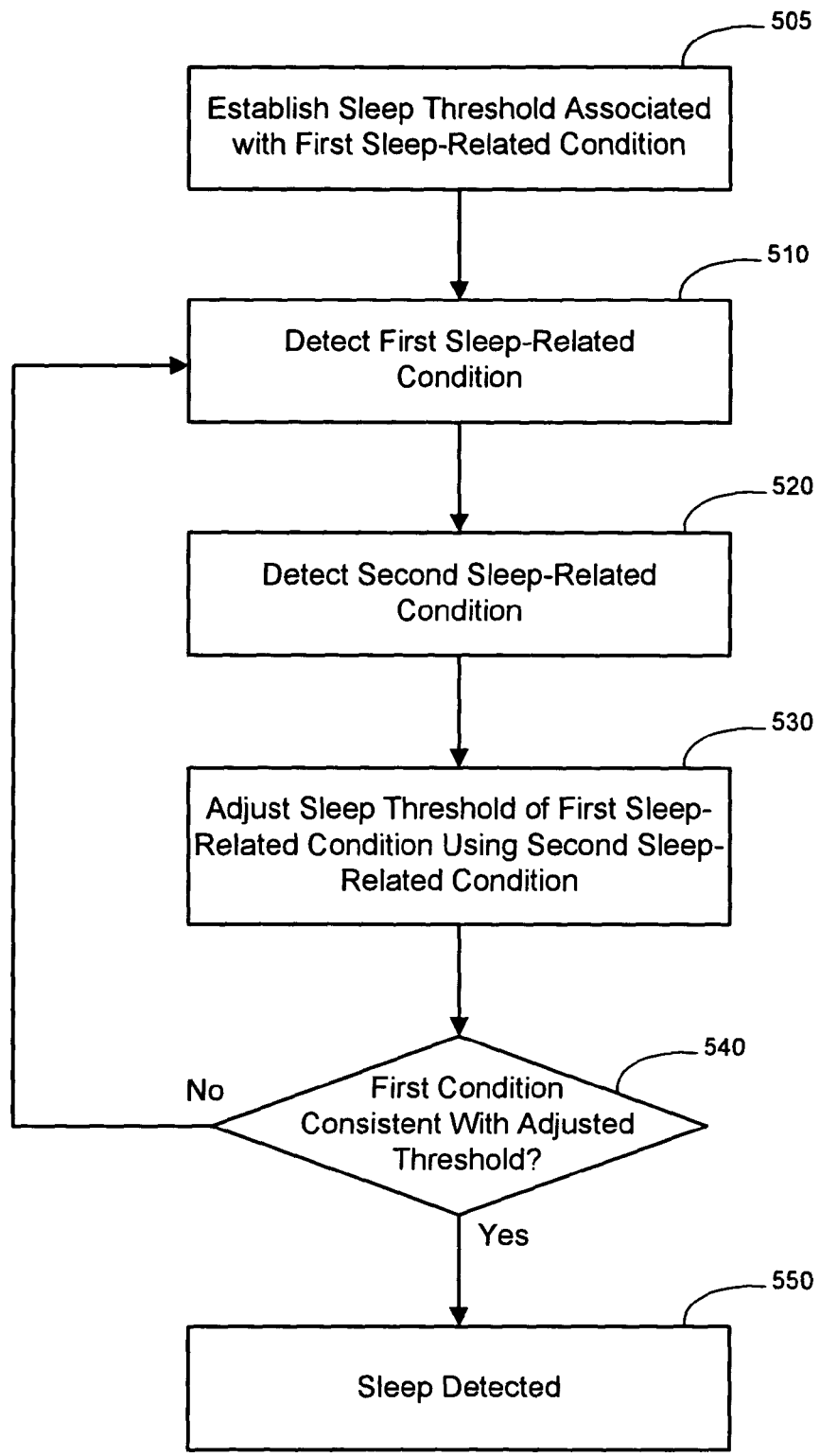
FIG. 5 is a flow chart illustrating a sleep detection method according to embodiments of the invention.

FIG. 5 is a flow chart illustrating a method of detecting sleep used in a sleep quality data system configured according to principles of the invention. A sleep threshold associated with a first sleep-related patient condition is established 505. The sleep threshold may be determined from clinical data of a sleep threshold acquired using a group of subjects, for example. The sleep threshold may also be determined using historical data taken from the particular patient for whom the sleep condition is to be detected.

First and second sleep-related conditions are detected 510, 520. The first and the second sleep-related conditions may be detected using sensors implanted in the patient, attached externally to the patient or located remote from the patient, for example, as previously described in connection with FIG. 3. The first and the second sleep-related conditions may include any condition associated with sleep and are not limited to the representative sleep-related conditions listed above.

The sleep threshold established for the first sleep-related condition is adjusted using the second sleep-related condition 530. For example, if the second sleep-related condition indicates a high level of activity that is incompatible with a sleep state, the sleep threshold of the first sleep-related condition may be adjusted downward to require sensing a decreased level of the first sleep-related condition before a sleep condition is detected.

If the first sleep-related condition is consistent with sleep according to the adjusted sleep threshold 540, sleep is detected 550. If the first sleep-related condition is not consistent with sleep using the adjusted sleep threshold, the first and the second sleep-related conditions continue to be detected 510, 520 and the threshold adjusted 530 until sleep is detected 550.

Figure 6:
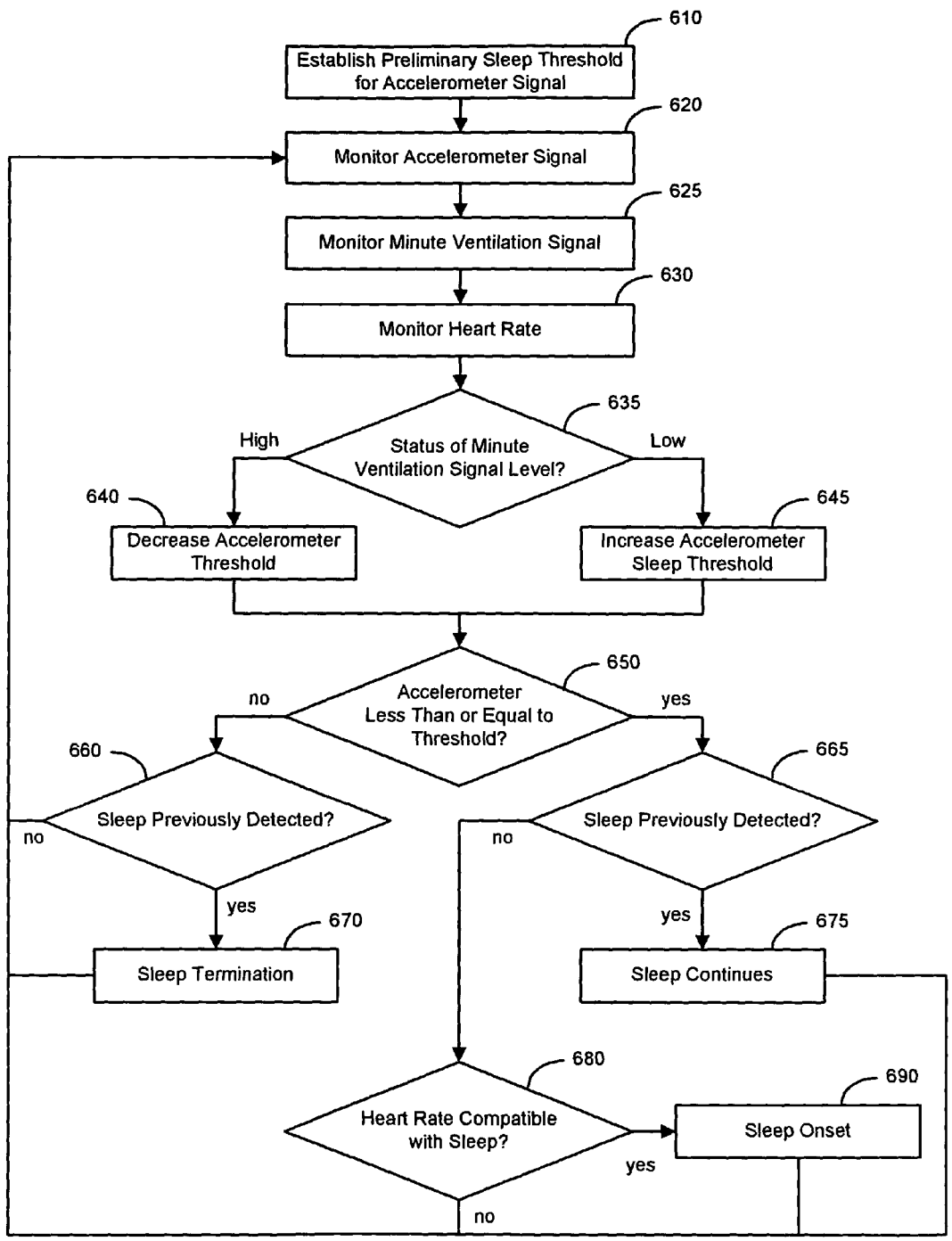
FIG. 6 is a flow chart illustrating a method for detecting sleep as a part of a sleep quality data collection approach according to embodiments of the invention.

The flow chart of FIG. 6 illustrates a method for detecting sleep using accelerometer and MV signals according to embodiments of the invention. In the method illustrated in FIG. 6, an accelerometer and a minute ventilation sensor are used to detect patient activity and patient respiration conditions, respectively. A preliminary sleep threshold is determined 610 with respect to the patient activity condition sensed by the accelerometer. The preliminary sleep threshold may be determined from clinical data derived from a group of subjects or from historical data taken from the patient over a period of time.

The activity condition of the patient is monitored 620 using an accelerometer that may be incorporated in an implantable cardiac rhythm management system as described in connection with FIG. 3. Alternatively, the accelerometer may be attached externally to the patient. The patient's MV condition is monitored 625, for example, using a transthoracic impedance sensor. A transthoracic impedance sensor may be implemented as a component of an implantable CRM device.

In this embodiment, the patient's activity represents the sleep detection condition and is compared to the sleep threshold. The patient's MV is used as the threshold adjustment condition to adjust the sleep threshold. In addition, in this example, the patient's heart rate is monitored 630 and used to provide a sleep confirmation condition.

The sleep threshold adjustment is accomplished using the patient's MV condition to adjust the activity sleep threshold. If the patient's MV condition is low relative to an expected MV level associated with sleep, the activity sleep threshold is increased. Similarly, if the patient's MV level is high relative to an expected MV level associated with sleep, the activity sleep threshold is decreased. Thus, when the patient's MV level is high, less activity is required to make the determination that the patient is sleeping. Conversely when the patient's MV level is relatively low, a higher activity level may result in detection of sleep. The use of two sleep-related conditions to determine the patient's sleep state enhances the accuracy of sleep detection over previous methods.

Various signal processing techniques may be employed to process the raw sensor signals. For example, a moving average of a plurality of samples of the sensor signals may be calculated. Furthermore, the sensor signals may be amplified, filtered, digitized or otherwise processed.

If the MV level is high 635 relative to an expected MV level associated with sleep, the activity sleep threshold is decreased 640. If the MV level is low 635 relative to an expected MV level associated with sleep, the activity sleep threshold is increased 645.

If the patient's activity level is less than or equal to the adjusted sleep threshold 650, and if the patient is currently in a sleep state 665, then the patient's heart rate is checked 680 to confirm that the patient is asleep. If the patient's heart rate is compatible with sleep 680, then sleep onset is determined 690. If the patient's heart rate is incompatible with sleep, then the patient's sleep-related conditions continue to be monitored.

If the patient's activity level is less than or equal to the adjusted sleep threshold 650 and if the patient is currently in a sleep state 665, then a continuing sleep state is determined and the patient's sleep-related conditions continue to be monitored for sleep termination to occur.

If the patient's activity level is greater than the adjusted sleep threshold 650 and the patient is not currently in a sleep state 660, then the patient's sleep-related conditions continue to be monitored until sleep onset is detected 690. If the activity level is greater than the adjusted sleep threshold 650 and the patient is currently in a sleep state 660, then sleep termination is detected 670.

Figure 7:
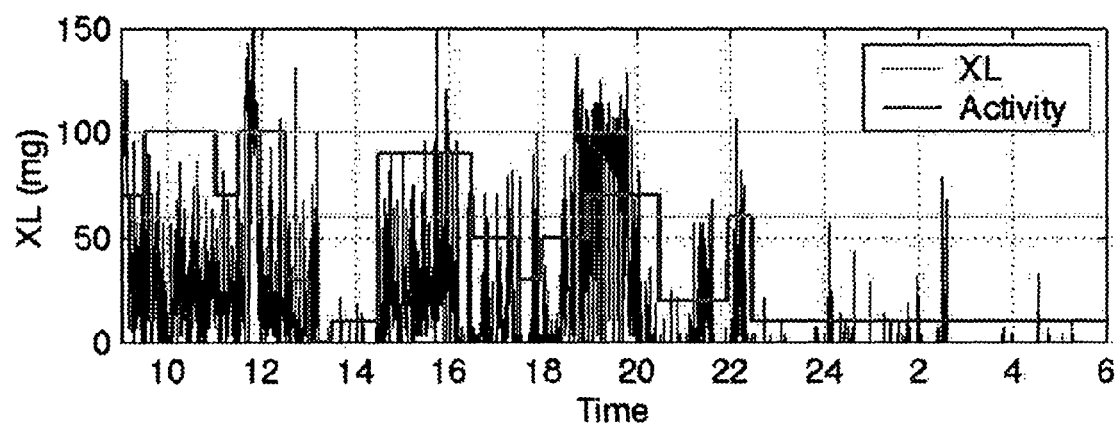
FIG. 7 is a graph of a patient's activity condition as indicated by an accelerometer signal.
Figure 8:
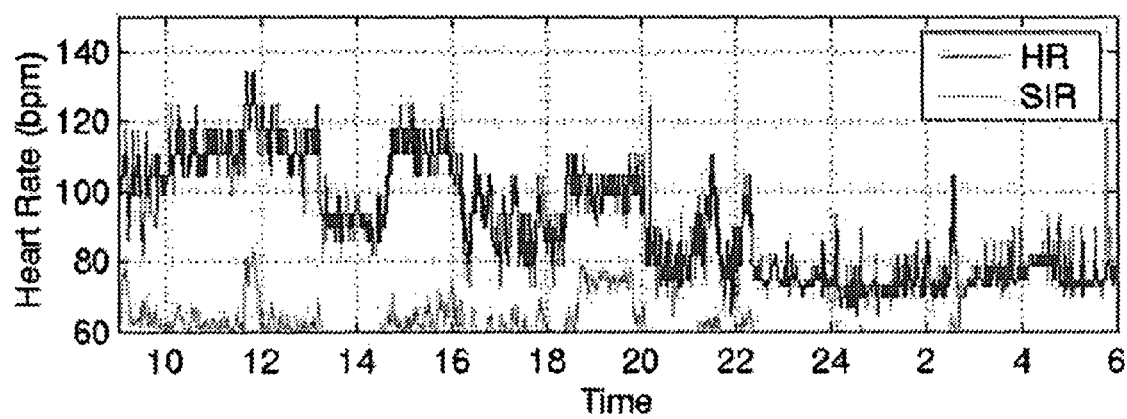
FIG. 8 is a graph of a patient's heart rate.

The graphs of FIGS. 7-10 illustrate the adjustment of the activity sleep threshold. The relationship between patient activity and the accelerometer and MV signals is trended over a period of time to determine relative signal levels associated with sleep. The graph of FIG. 7 illustrates the patient's activity as indicated by an accelerometer. The patient's heart rate for the same period is shown in the graph of FIG. 8. The accelerometer signal indicates a period of sleep associated with a relatively low level of activity beginning slightly before 23:00 and continuing through 6:00. The patient's heart rate appropriately tracks the activity level indicated by the accelerometer indicating a similar period of decreased heart rate corresponding to sleep. The signal level of the accelerometer during known periods of sleep may be used to establish a threshold for sleep detection.

Figure 9:
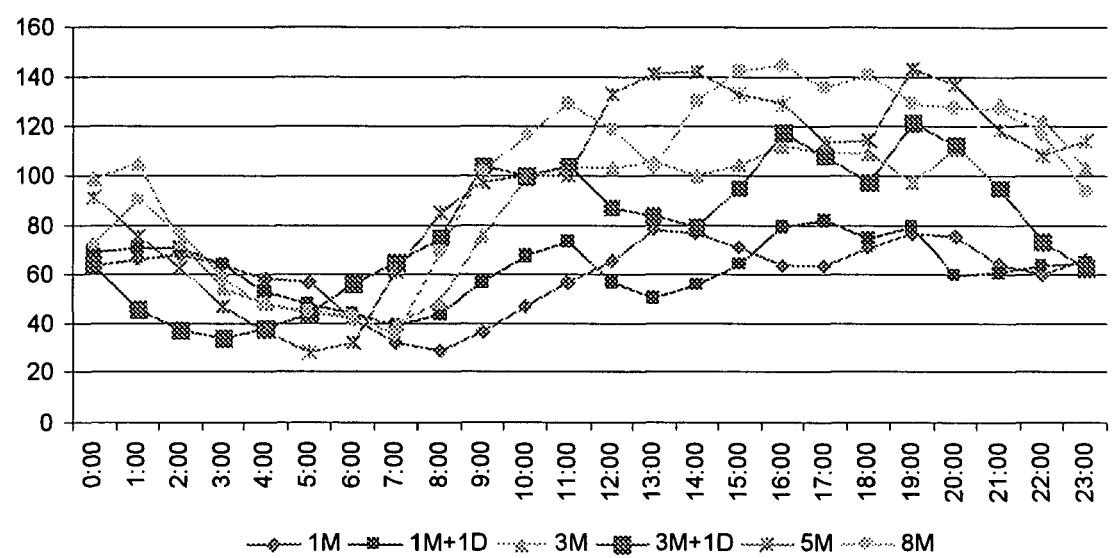
FIG. 9 is a graph of a patient's minute ventilation (MV) condition.

FIG. 9 is a graph of the patient's minute ventilation signal over time. Historical data of minute ventilation is graphed over an 8 month period. The minute ventilation data may be used to determine the minute ventilation signal level associated with sleep. In this example, a composite minute ventilation graph using the historical data presents a roughly sinusoidal shape with the relatively low minute ventilation levels occurring during the period approximately from hours 21:00 through 8:00. The decreased minute ventilation level is associated with periods of sleep. The minute ventilation level associated with sleep is used to implement sleep threshold adjustment.

Figure 10:
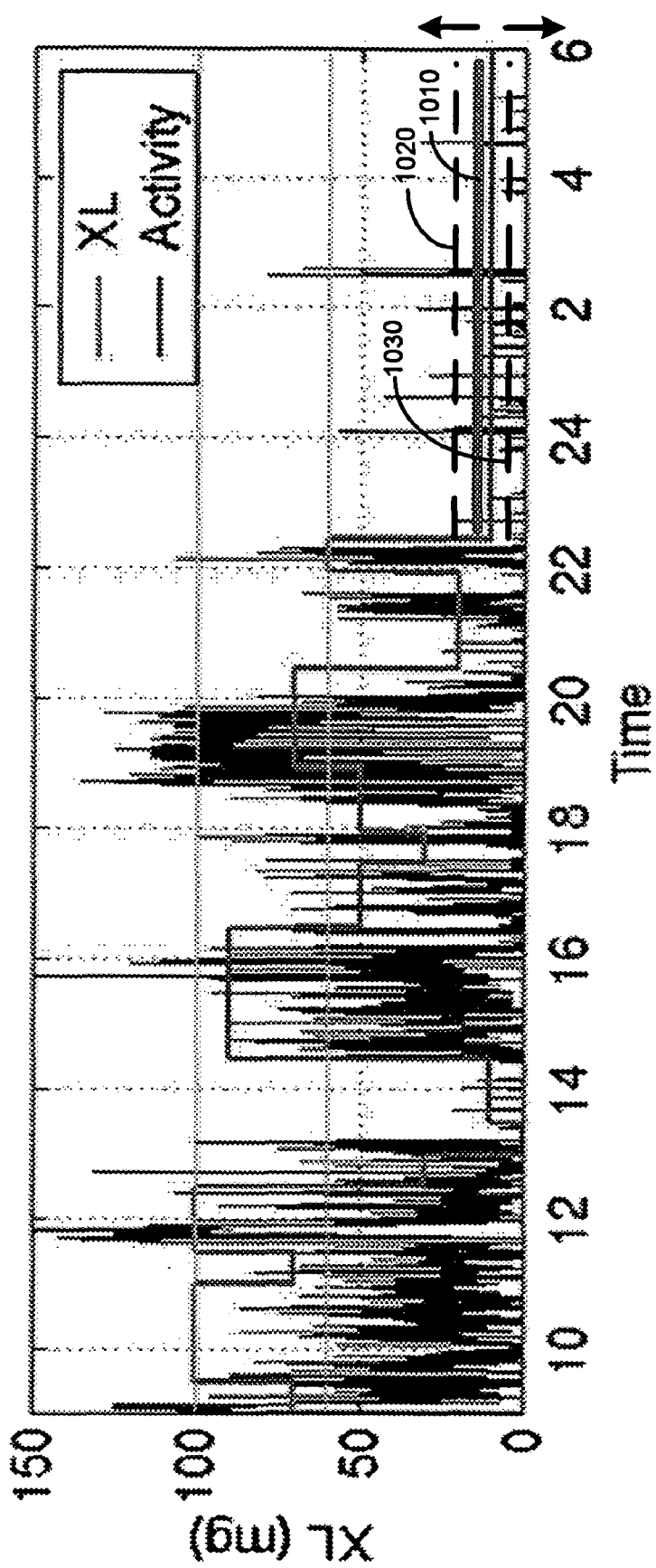
FIG. 10 illustrates adjustment of a sleep threshold in accordance with embodiments of the invention.

FIG. 10 illustrates adjustment of the activity sleep threshold using the MV data. The initial sleep threshold 1010 is established using the baseline activity data acquired as discussed above. If the patient's MV level is low relative to an expected MV level associated with sleep, the activity sleep threshold is increased 1020. If the patient's MV level is high relative to an expected MV level associated with sleep, the activity sleep threshold is decreased 1030. When the patient's MV level is high, less activity detected by the accelerometer is required to make the determination that the patient is sleeping. However, if the patient's MV level is relatively low, a higher activity level may result in detection of sleep. The use of two sleep-related signals to establish and adjust a sleep threshold enhances the accuracy of sleep detection over previous methods.

Additional sleep-related conditions may be sensed and used to improve the sleep detection method described above. For example, a posture sensor may be used to detect the posture of the patient and used to confirm sleep. If the posture sensor signal indicates an upright posture, then the posture sensor signal may be used to override a determination of sleep using the sleep detection and threshold adjustment conditions. Other conditions may also be used in connection with sleep determination or confirmation, including the representative set of sleep-related conditions indicated above. In another example, a proximity to bed sensor may be used alone or in combination with a posture sensor to detect that the patient is in bed and is lying down.

A sleep detection system may detect sleep onset, termination, arousals as well as the sleep stages, including REM and non-REM sleep. REM sleep may be discriminated from NREM sleep, for example, by examining one or more signals indicative of REM, e.g., muscle atonia, rapid eye movements, or EEG signals. Methods and systems for detecting REM sleep that are particularly useful for patients with implantable devices are discussed in commonly owned U.S. Publication No. 2005/0043652 and incorporated herein by reference. Various conditions indicative of sleep state may be detected using sensors, e.g., electroencephalogram (EEG), electrooculogram (EOG), or electromyogram (EMG) sensors, coupled through wired or wireless connections to the sleep detection circuitry. The sleep detection circuitry may analyze the various patient conditions sensed by the sensors to track the patient's sleep through various sleep states, including REM and NREM stages.

Returning to FIG. 3, the sleep quality data system 300 may also employ disordered breathing detection circuitry 342 to detect episodes of disordered breathing. Disordered breathing may be detected in numerous ways using one or more of the patient conditions listed in Table 1. Methods and systems for detecting disordered breathing are described in commonly owned U.S. Pat. No. 7,252,640, which is incorporated herein by reference. According to this approach, disordered breathing may be detected by examining characteristics of the patient's respiration patterns to determine if the respiration patterns are consistent with disordered breathing.

Figure 11:
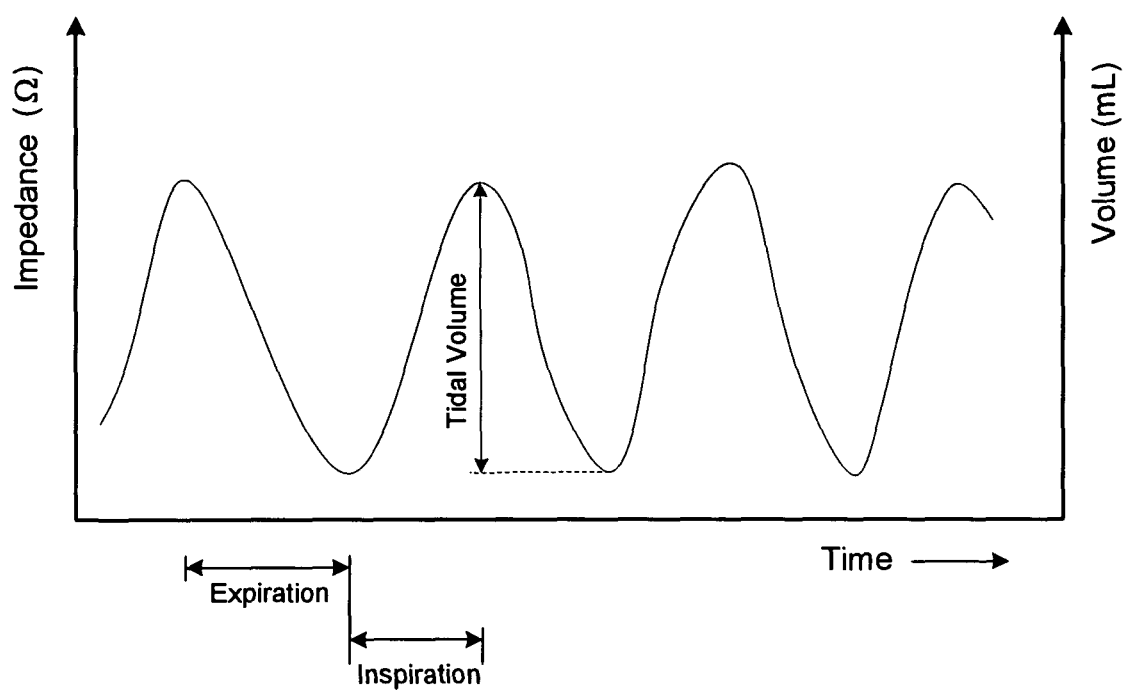
FIG. 11 illustrates a normal respiration pattern as represented by a transthoracic impedance sensor signal.

FIG. 11 illustrates a normal respiration pattern as represented by a transthoracic impedance sensor signal. The transthoracic impedance increases during respiratory inspiration and decreases during respiratory expiration. During NREM sleep, a normal respiration pattern includes regular, rhythmic inspiration—expiration cycles without substantial interruptions.

Figure 12:
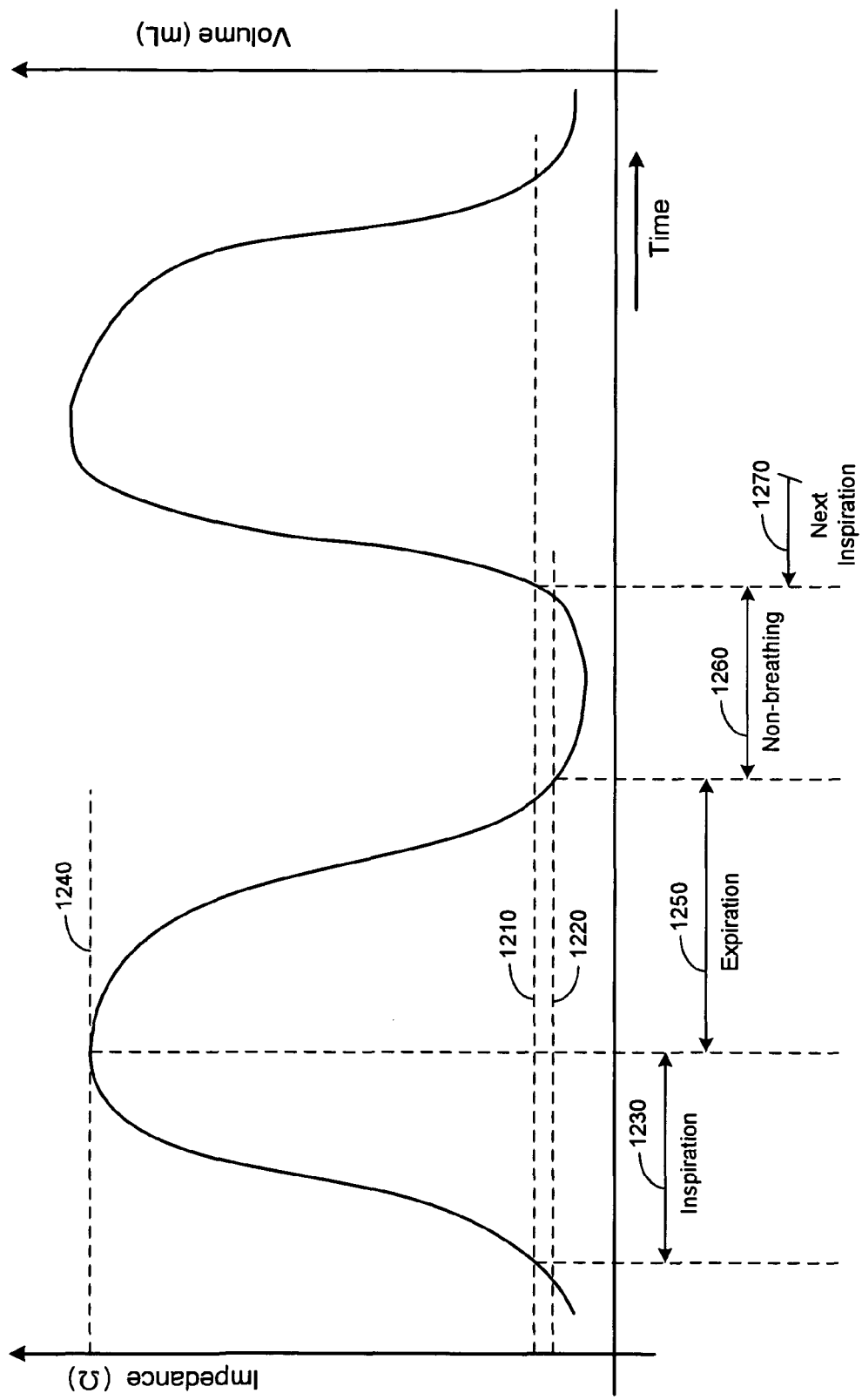
FIG. 12 illustrates respiration intervals used for disordered breathing detection according to embodiments of the invention.

In one embodiment, detection of disordered breathing, including, for example, sleep apnea and hypopnea, involves defining and examining a number of respiratory cycle intervals. FIG. 12 illustrates respiration intervals used for disordered breathing detection according to an embodiment of the invention. A respiration cycle is divided into an inspiration period corresponding to the patient inhaling, an expiration period, corresponding to the patient exhaling, and a non-breathing period occurring between inhaling and exhaling.

Respiration intervals are established using inspiration 1210 and expiration 1220 thresholds. The inspiration threshold 1210 marks the beginning of an inspiration period 1230 and is determined by the transthoracic impedance signal rising above the inspiration threshold 1210. The inspiration period 1230 ends when the transthoracic impedance signal is maximum 1240. A maximum transthoracic impedance signal 1240 corresponds to both the end of the inspiration interval 1230 and the beginning of the expiration interval 1250. The expiration interval 1250 continues until the transthoracic impedance falls below an expiration threshold 1220. A non-breathing interval 1260 starts from the end of the expiration period 1250 and continues until the beginning of the next inspiration period 1270.

Figure 13:
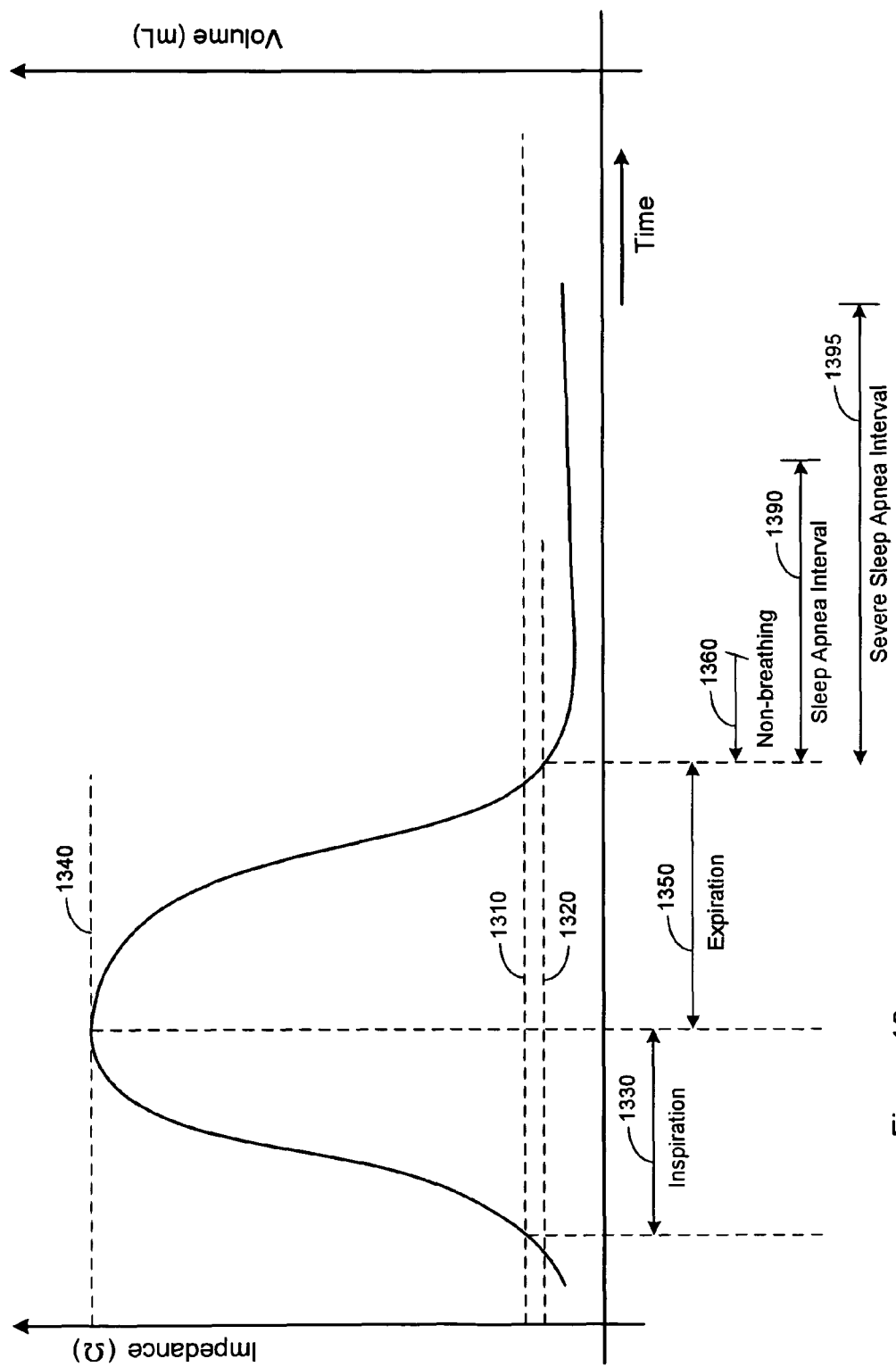
FIG. 13 illustrates detection of sleep apnea and severe sleep apnea according to embodiments of the invention.

Detection of sleep apnea and severe sleep apnea according to embodiments of the invention is illustrated in FIG. 13. The patient's respiration signals are monitored and the respiration cycles are defined according to inspiration 1330, expiration 1350, and non-breathing 1360 intervals as described in connection with FIG. 12. A condition of sleep apnea is detected when a non-breathing period 1360 exceeds a first predetermined interval 1390, denoted the sleep apnea interval. A condition of severe sleep apnea is detected when the non-breathing period 1360 exceeds a second predetermined interval 1395, denoted the severe sleep apnea interval. For example, sleep apnea may be detected when the non-breathing interval exceeds about 10 seconds, and severe sleep apnea may be detected when the non-breathing interval exceeds about 20 seconds.

Figure 14A:
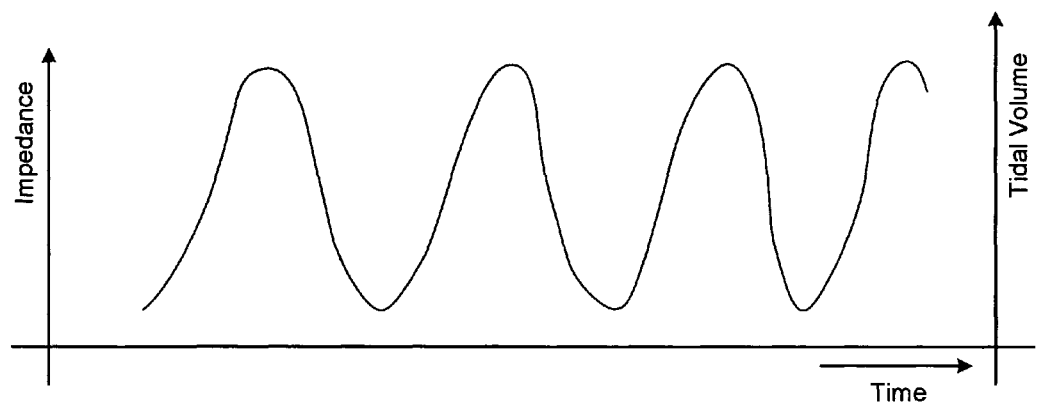
FIGS. 14A-B are graphs of tidal volume derived from transthoracic impedance measurements according to embodiments of the invention.
Figure 14B:
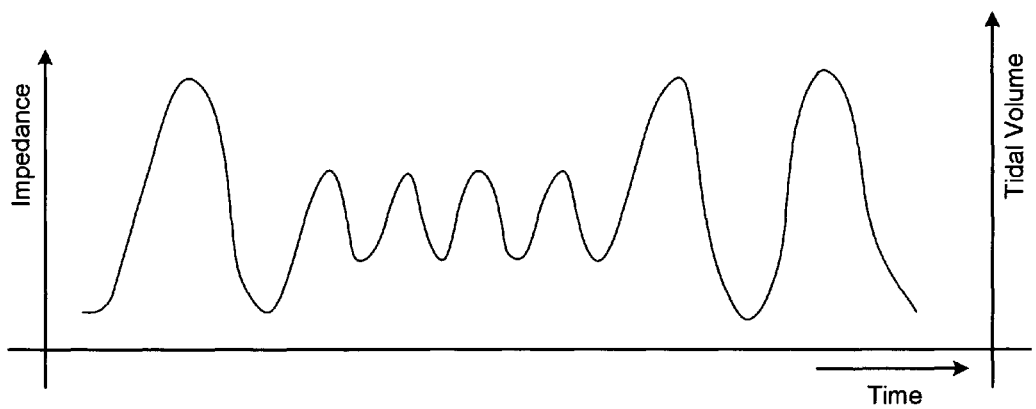

Hypopnea is a condition of disordered breathing characterized by abnormally shallow breathing. FIGS. 14A-B are graphs of respiration patterns derived from transthoracic impedance measurements. The graphs compare the tidal volume of a normal breathing cycle to the tidal volume of a hypopnea episode. FIG. 14A illustrates normal respiration tidal volume and rate. As shown in FIG. 14B, hypopnea involves a period of abnormally shallow respiration.

According to an embodiment of the invention, hypopnea is detected by comparing a patient's respiratory tidal volume to a hypopnea tidal volume threshold. The tidal volume for each respiration cycle may be derived from transthoracic impedance measurements. The hypopnea tidal volume threshold may be established using clinical results providing a representative tidal volume and duration for hypopnea events. In one configuration, hypopnea is detected when an average of the patient's respiratory tidal volume taken over a selected time interval falls below the hypopnea tidal volume threshold.

Figure 15:
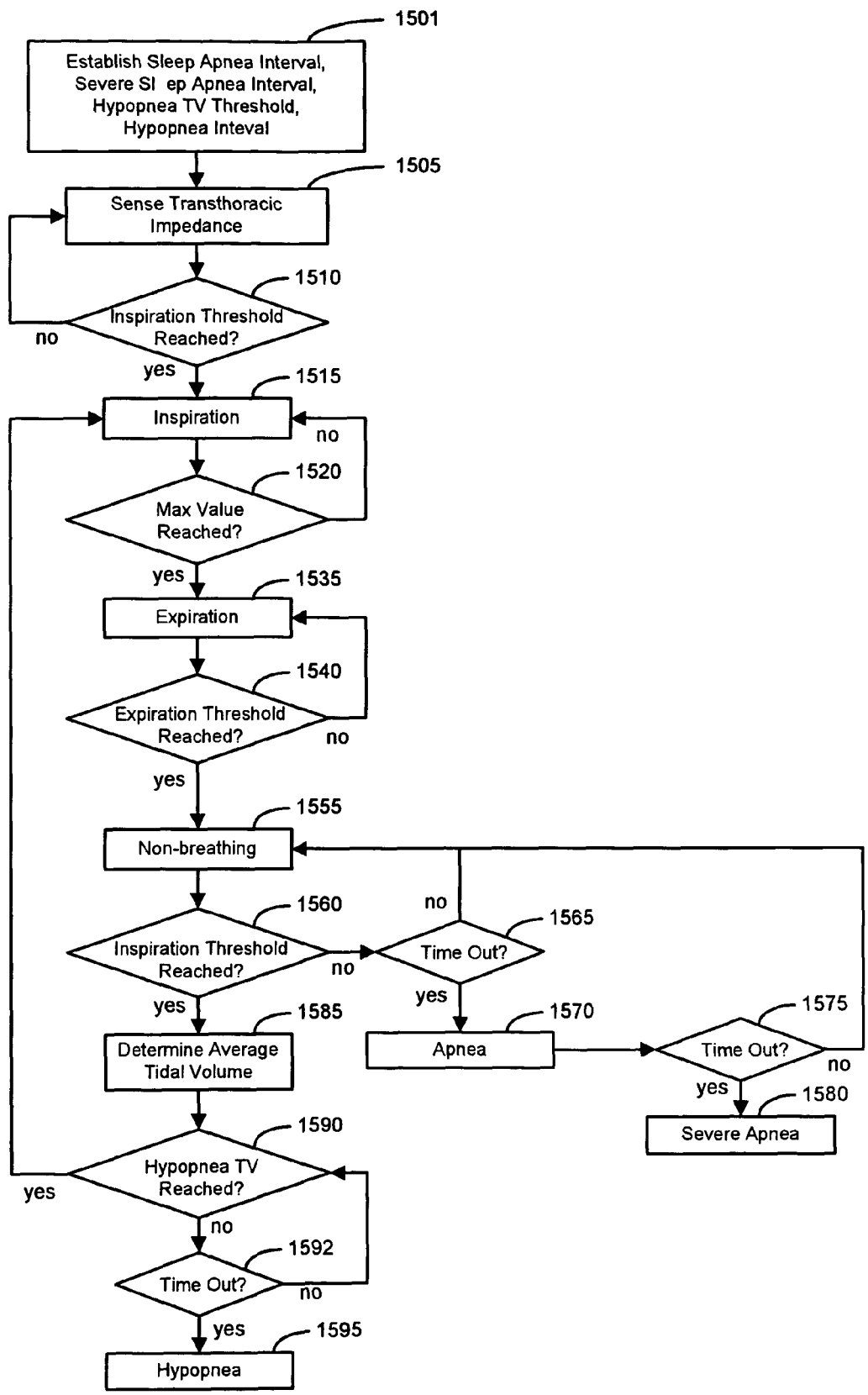
FIG. 15 is a flow chart illustrating a method of apnea and hypopnea detection according to embodiments of the invention.

FIG. 15 is a flow chart illustrating a method of apnea and/or hypopnea detection according to embodiments of the invention. Various parameters are established 1501 before analyzing the patient's respiration for disordered breathing episodes, including, for example, inspiration and expiration thresholds, sleep apnea interval, severe sleep apnea interval, and hypopnea tidal volume threshold.

The patient's transthoracic impedance is detected 1505. If the transthoracic impedance exceeds 1510 the inspiration threshold, the beginning of an inspiration interval is detected 1515. If the transthoracic impedance remains below 1510 the inspiration threshold, then the impedance signal is checked 1505 periodically until inspiration 1515 occurs.

During the inspiration interval, the patient's transthoracic impedance is monitored until a maximum value of the transthoracic impedance is detected 1520. Detection of the maximum value signals an end of the inspiration period and a beginning of an expiration period 1535.

The expiration interval is characterized by decreasing transthoracic impedance. When the transthoracic impedance falls below 1540 the expiration threshold, a non-breathing interval is detected 1555.

If the transthoracic impedance does not exceed 1560 the inspiration threshold within a first predetermined interval 1565, denoted the sleep apnea interval, then a condition of sleep apnea is detected 1570. Severe sleep apnea is detected 1580 if the non-breathing period extends beyond a second predetermined interval 1575, denoted the severe sleep apnea interval.

When the transthoracic impedance exceeds 1560 the inspiration threshold, the tidal volume from the peak-to-peak transthoracic impedance is calculated 1585. The peak-to-peak transthoracic impedance provides a value proportional to the tidal volume of the respiration cycle. This value is compared 1590 to a hypopnea tidal volume threshold. If the peak-to-peak transthoracic impedance is consistent with 1590 the hypopnea tidal volume threshold for a predetermined time 1592, then a hypopnea cycle is detected 1595.

Additional sensors, such as motion sensors and/or posture sensors, may be used to confirm or verify the detection of a sleep apnea or hypopnea episode. The additional sensors may be employed to prevent false or missed detections of sleep apnea or hypopnea due to posture and/or motion related artifacts.

Another embodiment of the invention involves classifying respiration patterns as disordered breathing episodes based on the breath intervals and/or tidal volumes of one or more respiration cycles within the respiration patterns. According to this embodiment, the duration and tidal volumes associated with a respiration pattern are compared to duration and tidal volume thresholds. The respiration pattern may be determined to represent a disordered breathing episode based on the comparison.

Figure 16:
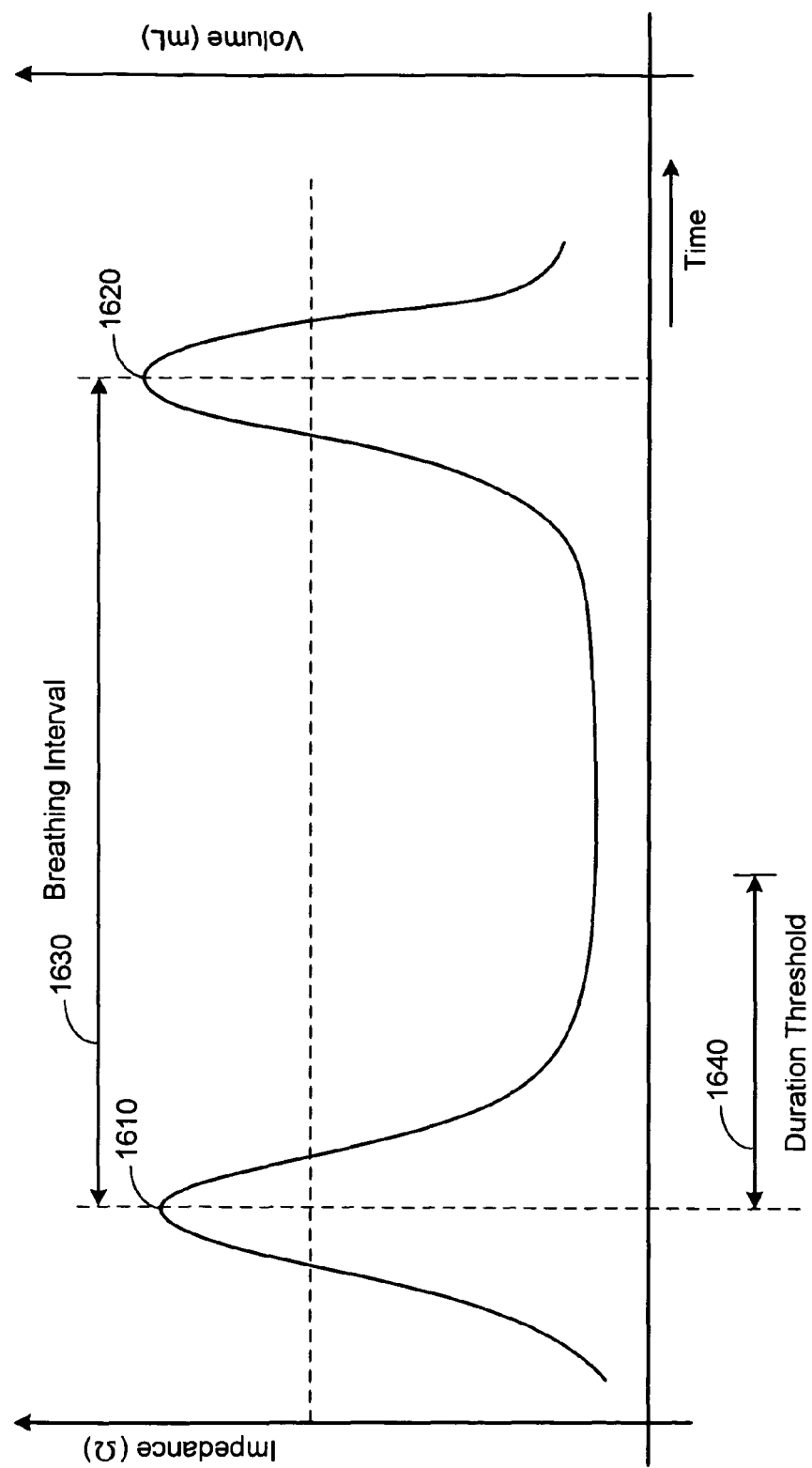
FIG. 16 is a graph illustrating a breathing interval according to embodiments of the invention.

According to this embodiment, a breath interval 1630 is established for each respiration cycle. A breath interval represents the interval of time between successive breaths, as illustrated in FIG. 16. A breath interval 1630 may be defined in a variety of ways, for example, as the interval of time between successive maxima 1610, 1620 of the impedance signal waveform.

Detection of disordered breathing, in accordance with methods of the invention, involves the establishment of a duration threshold and a tidal volume threshold. If a breath interval exceeds the duration threshold, an apnea event is detected. Detection of sleep apnea, in accordance with this embodiment, is illustrated in the graph of FIG. 16. Apnea represents a period of non-breathing. A breath interval 1630 exceeding a duration threshold 1640 comprises an apnea episode.

Hypopnea may be detected using a duration threshold and a tidal volume threshold. A hypopnea event represents a period of shallow breathing greater than the duration threshold. Each respiration cycle in a hypopnea event is characterized by a tidal volume less than the tidal volume threshold. Further, the decreased tidal volume cycles persist longer than the duration threshold.

Figure 17:
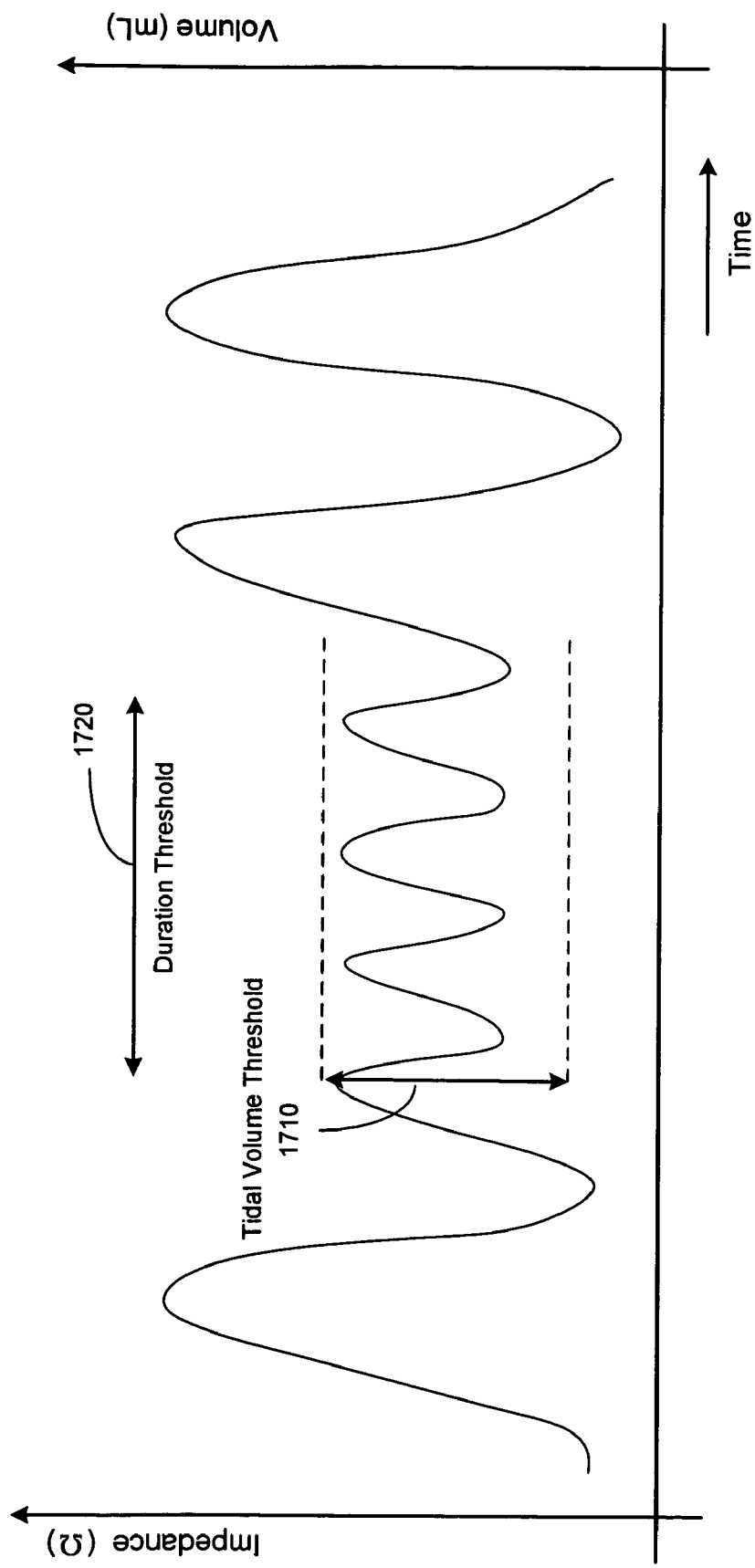
FIG. 17 is a graph illustrating a hypopnea detection approach in accordance with embodiments of the invention.

A hypopnea detection approach, in accordance with embodiments of the invention, is illustrated in FIG. 17. Shallow breathing is detected when the tidal volume of one or more breaths is below a tidal volume threshold 1710. If the shallow breathing continues for an interval greater than a duration threshold 1720, then the breathing pattern represented by the sequence of shallow respiration cycles, is classified as a hypopnea event.

Figure 18A:
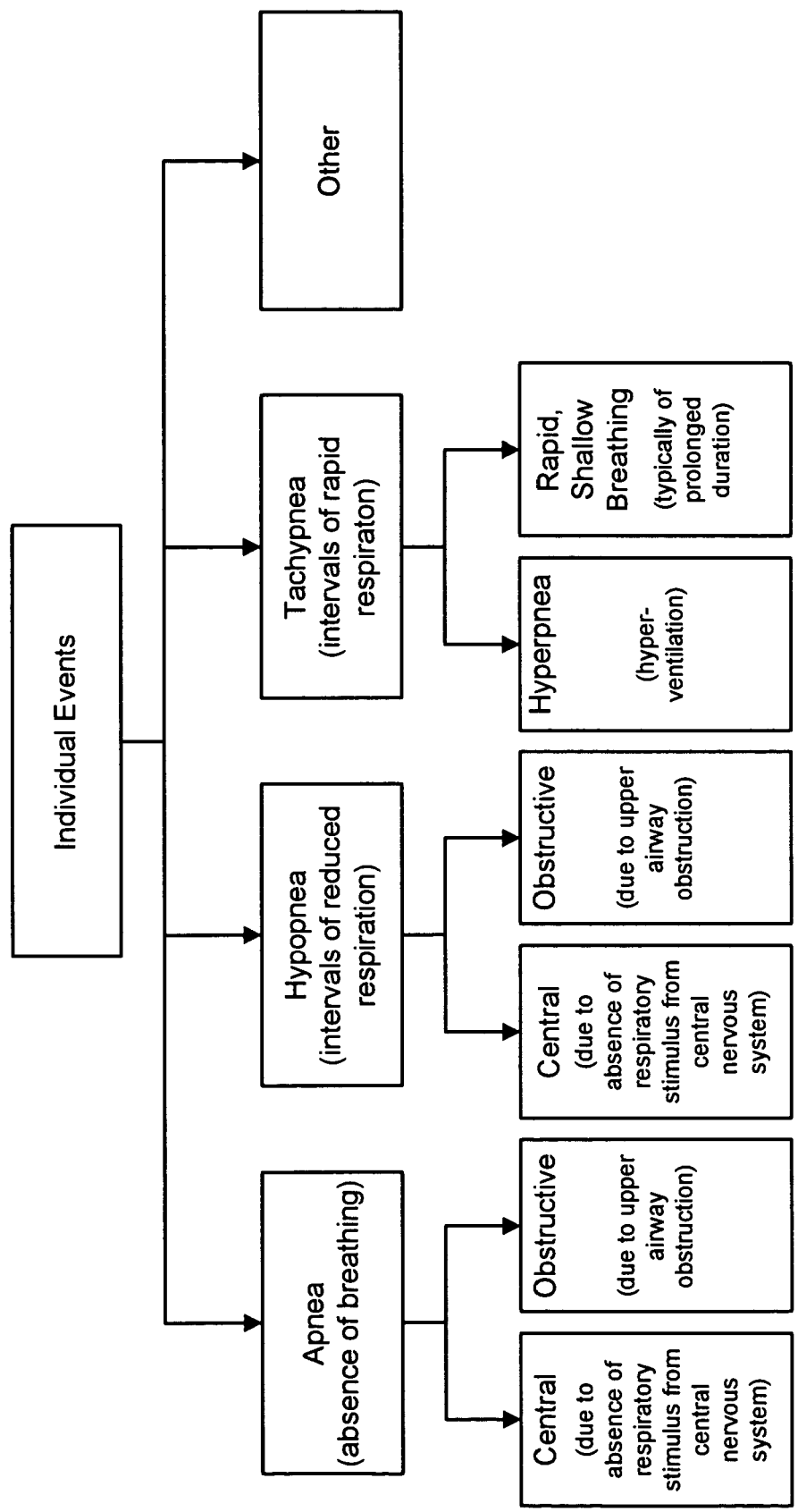
FIGS. 18A-B are charts illustrating nomenclature for individual disordered breathing events and combinations of disordered breathing events, respectively.
Figure 18B:
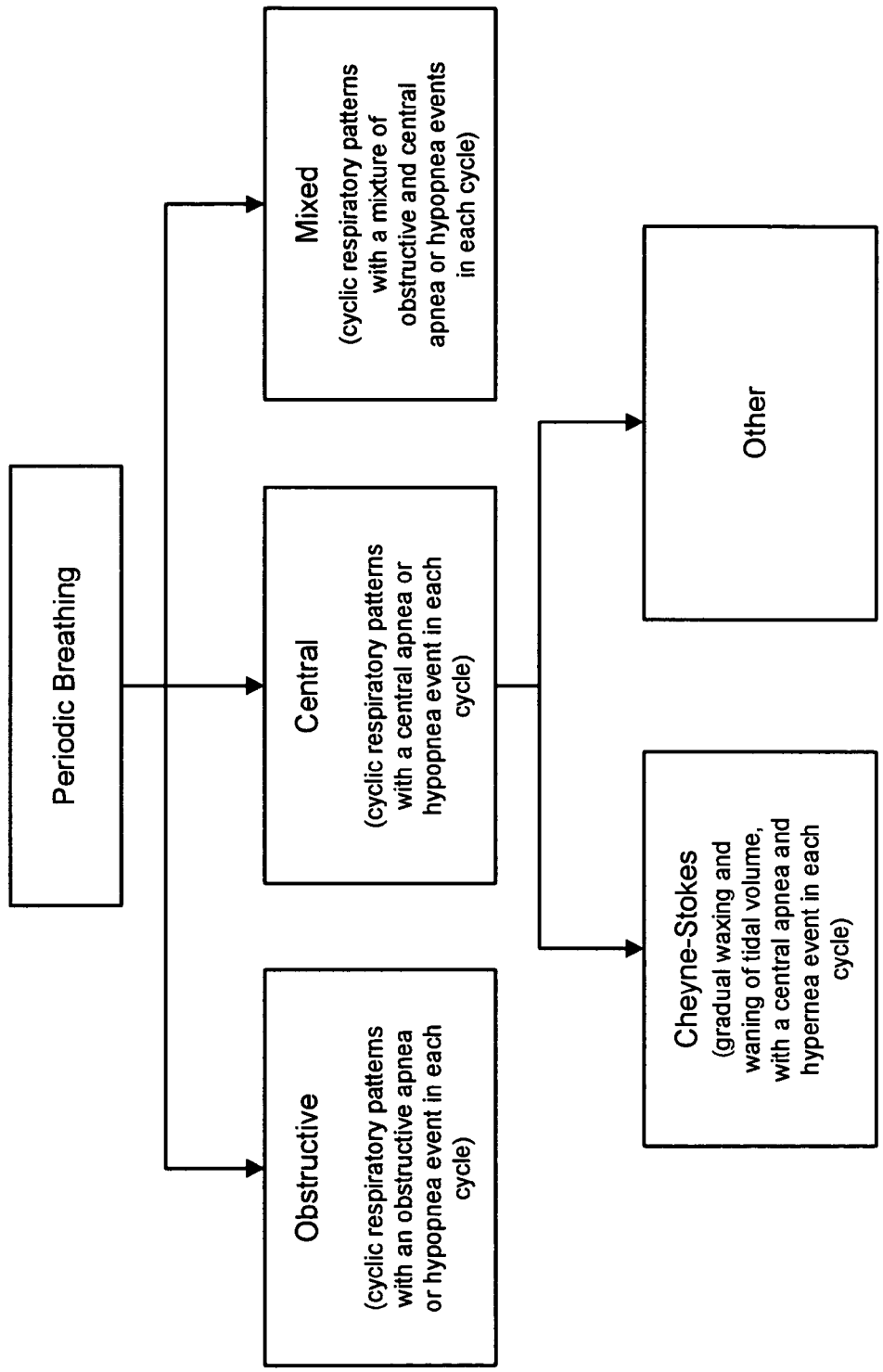

FIGS. 18A and 18B provide charts illustrating classification of individual disordered breathing events and combination of periodic breathing events, respectively. As illustrated in FIG. 18A, individual disordered breathing events may be grouped into apnea, hypopnea, tachypnea and other disordered breathing events. Apnea events are characterized by an absence of breathing. Intervals of reduced respiration are classified as hypopnea events. Tachypnea events include intervals of rapid respiration characterized by an elevated respiration rate.

As illustrated in FIG. 18A, apnea and hypopnea events may be further subdivided as either central events, e.g., caused either by central nervous system dysfunction, or obstructive events, e.g., caused by upper airway obstruction. A tachypnea event may be further classified as a hyperpnea event, represented by rapid deep breathing (hyperventilation). A tachypnea event may alternatively be classified as rapid shallow breathing, typically of prolonged duration.

FIG. 18B illustrates classification of periodic disordered breathing events. Periodic breathing may be classified as obstructive, central or mixed. Obstructive periodic breathing is characterized by cyclic respiratory patterns with an obstructive apnea or hypopnea event in each cycle. In central periodic breathing, the cyclic respiratory patterns include a central apnea or hypopnea event in each cycle. Periodic breathing may also be of mixed origin. In this case, cyclic respiratory patterns have a mixture of obstructive and central apnea events in each cycle. Cheyne-Stokes respiration is a particular type of periodic breathing characterized by a gradual waxing and waning of tidal volume and having a central apnea and hyperpnea event in each cycle. Other manifestations of periodic breathing are also possible.

As illustrated in FIGS. 18C-G, a respiration pattern detected as a disordered breathing episode may include only an apnea respiration cycle 1810 (FIG. 18C), only hypopnea respiration cycles 1850 (FIG. 18F), or a mixture of hypopnea and apnea respiration cycles 1820 (FIG. 18D), 1830 (FIG. 18E), 1860 (FIG. 18G). A disordered breathing event 1820 may begin with an apnea respiration cycle and end with one or more hypopnea cycles. In another pattern, the disordered breathing event 1830 may begin with hypopnea cycles and end with an apnea cycle. In yet another pattern, a disordered breathing event 1860 may begin and end with hypopnea cycles with an apnea cycle in between the hypopnea cycles. Analysis of the characteristic respiration patterns associated with various types of disordered breathing may be used to detect, classify and evaluate disordered breathing episodes.

Figure 19:
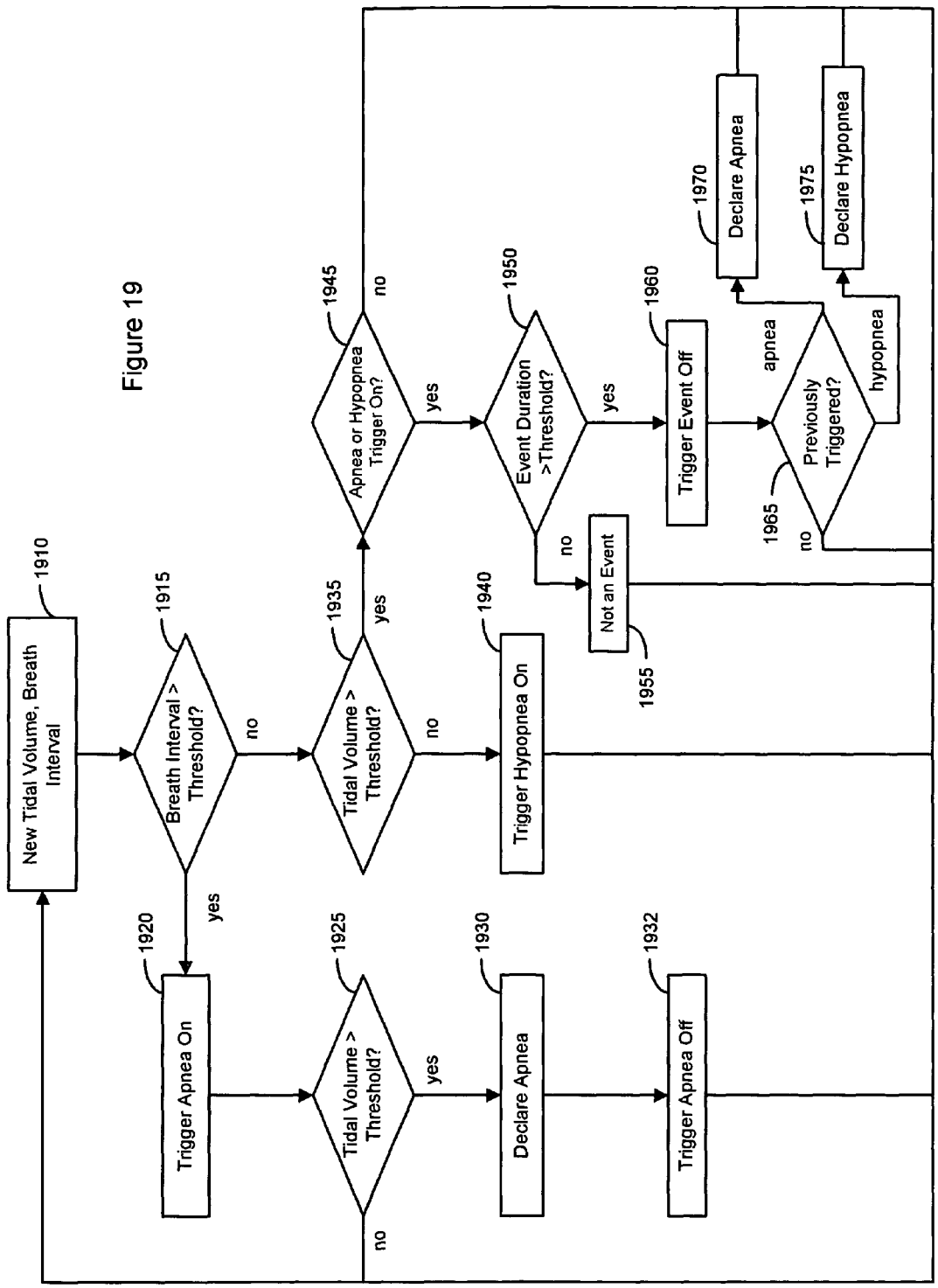
FIG. 19 is a flow chart of a method for detecting disordered breathing by classifying breathing patterns in accordance with embodiments of the invention.

FIG. 19 is a flow chart of a method for detecting disordered breathing by classifying breathing patterns using breath intervals in conjunction with tidal volume and duration thresholds as previously described above. In this example, a duration threshold and a tidal volume threshold are established for determining both apnea and hypopnea breath intervals. An apnea episode is detected if the breath interval exceeds the duration threshold. A hypopnea episode is detected if the tidal volume of successive breaths remains less than the tidal volume threshold for a period in excess of the duration threshold. Mixed apnea/hypopnea episodes may also occur. In these cases, the period of disordered breathing is characterized by shallow breaths or non-breathing intervals. During the mixed apnea/hypopnea episodes, the tidal volume of each breath remains less than the tidal volume threshold for a period exceeding the duration threshold.

The patient's respiration cycles are determined, for example, using transthoracic impedance signals. Each breath 1910 is characterized by a breath interval, i.e., the interval of time between two impedance signal maxima and a tidal volume (TV). If a breath interval exceeds 1915 the duration threshold, then the respiration pattern is consistent with an apnea event, and an apnea event trigger is turned on 1920. If the tidal volume of the breath interval exceeds 1925 the tidal volume threshold, then the breathing pattern is characterized by two respiration cycles of normal volume separated by a non-breathing interval. This pattern represents a purely apneic disordered breathing event, and apnea is detected 1930. Because the final breath of the breath interval was normal, the apnea event trigger is turned off 1932, signaling the end of the disordered breathing episode. However, if the tidal volume of the breath interval does not exceed 1925 the tidal volume threshold, the disordered breathing period is continuing and the next breath is checked 1910.

If the breath interval does not exceed 1915 the duration threshold, then the tidal volume of the breath is checked 1935. If the tidal volume does not exceed 1935 the tidal volume threshold, the breathing pattern is consistent with a hypopnea cycle and a hypopnea event trigger is set on 1940. If the tidal volume exceeds the tidal volume threshold, then the breath is normal.

If a period of disordered breathing is in progress, detection of a normal breath signals the end of the disordered breathing. If disordered breathing was previously detected 1945, and if the disordered breathing event duration has not exceeded 1950 the duration threshold, and the current breath is normal, then no disordered breathing event is detected 1955. If disordered breathing was previously detected 1945, and if the disordered breathing event duration has extended for a period of time exceeding 1950 the duration threshold, and the current breath is normal, then the disordered breathing trigger is turned off 1960. In this situation, the duration of the disordered breathing episode was of sufficient duration to be classified as a disordered breathing episode. If an apnea event was previously triggered 1965, then an apnea event is declared 1970. If a hypopnea was previously triggered 1965, then a hypopnea event is declared 1975.

As previously discussed in connection with FIG. 3, a sleep quality analysis unit 340 may incorporate an abnormal nocturnal movement detector 344 to evaluate the movements of a patient during the night to detect nocturnal movement disorders such as RLS, PLMD, and/or bruxism. The patient may be instrumented with accelerometers located on the limbs or jaw, for example, to sense patient movement. Excessive movement, or movements having a characteristic pattern, e.g., periodic limb or jaw movements, may be classified as abnormal nocturnal movements. For example, bruxism is a sleep disorder wherein the patient grinds his teeth during sleep. An accelerometer attached to the patient's jaw may be used to sense movement of the jaw. Signals from the jaw accelerometer may be transferred to the abnormal movement detector for evaluation to determine if the movements are excessive or unusually periodic, indicating bruxism. In a similar application, accelerometers attached to the patient's limbs may generate signals used by the abnormal movement detector 344 to detect and classify disorders such as RLS and PLMD.

Figure 20:
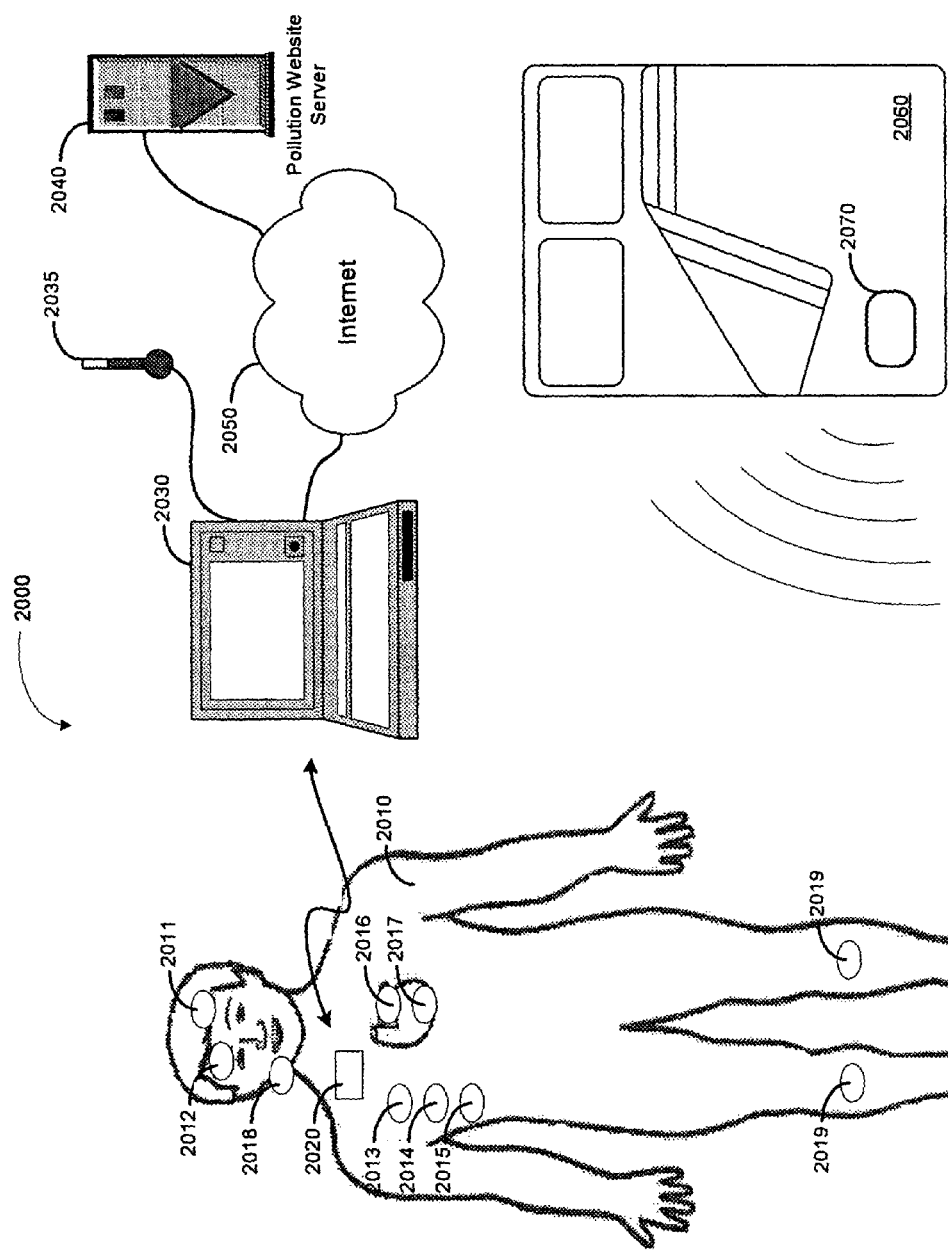
FIG. 20 illustrates a patient instrumented with components of a sleep quality data system according to embodiments of the invention.

FIG. 20 illustrates a patient 2010 instrumented with a sleep quality data system 2000 according to embodiments of the invention. The sleep quality data system collects sleep quality data from the patient using a number of sensors 2011-2019. In one configuration, the collected data is analyzed by a sleep quality analysis unit that may be an integrated component of an implantable sleep quality data collection and analysis unit 2020. In another configuration, the collected data may be downloaded to a patient-external device 2030 for storage, analysis, or display.

In the implementation illustrated in FIG. 20, the sleep quality data system 2000 includes an implantable sleep quality data collection and analysis unit 2020 coupled to a number of sensors 2011-2019. In this example, the sensors include an EGM sensor 2016 for detecting heart rate and heart rate variability conditions. A transthoracic impedance sensor 2017 is used to detect the respiration conditions of the patient, including, for example, minute ventilation, respiration rate, and tidal volume. An activity detector, e.g., accelerometer, 2015 may be used to detect patient activity conditions. The sleep quality data system detects patient conditions including the patient's posture and location using a posture sensor 2014 and a proximity to bed sensor 2013, respectively. The sleep quality data system senses the patient's brain activity using EEG sensors 2011 and the patient's eye movements using EOG sensors 2012. Jaw and limb movements are sensed using accelerometers attached to the patient's jaw 2018 and legs 2019.

In this application, the sleep quality data collection and analysis unit 2020 is configured to track the patient's heart rate, heart rate variability, minute ventilation, respiration rate, tidal volume, posture, proximity to bed, brain activity, eye movements, jaw movements and leg movements. At periodic intervals, the system samples signals from the sensors and stores data regarding the detected conditions in memory circuitry within the sleep quality data collection and analysis unit 2020. The sleep quality data collection and analysis unit 2020 may additionally access an external input unit 2030 to detect patient reported conditions, for example, recent tobacco and medication use by the patient. Further, the sleep quality data collection and analysis unit 2020 may monitor conditions using one or more external sensors. In the illustrated example, a thermometer 2035 is coupled through the external programmer 2030 and a pollution website 2040 is accessible to the sleep quality data collection and analysis unit 2020 through the internet 2050.

The sleep quality data collection and analysis unit 2020 may operate to acquire data during periods of both sleep and wakefulness. It may be beneficial, for example, to track changes in particular conditions measured during periods of wakefulness that are associated with sleep disordered breathing. For example, some patients who suffer from sleep apnea experience changes in heart rate variability, blood pressure variability, and/or sympathetic nerve activity during periods of wakefulness. Detection and analysis of the physiological changes attributable to sleep disorders and measurable during the time the patient is awake provides a more complete picture of sleep quality.

In another example, the patient's sleep quality may be evaluated by determining the patient's activity level while the patient is awake. The activity level of the patient during the day may provide important information regarding the patient's sleep quality. For example, if the patient is very inactive during periods of wakefulness, this may indicate that the patient's sleep is of inadequate quality or duration. Such information may also be used in connection with assessing the efficacy of a particular sleep disorder therapy and/or adjusting the patient's sleep disorder therapy. Methods and systems for determining the patient's activity level and generally assessing the well-being of a patient are described in commonly owned U.S. Pat. No. 6,021,351 which is incorporated herein by reference.

The analysis unit 2020 may calculate one or more sleep quality metrics quantifying the patient's sleep quality. A representative set of the sleep quality metrics include, for example, sleep efficiency, sleep fragmentation, number of arousals per hour, denoted the arousal index (AI).

The analysis unit 2020 may also compute one or more metrics quantifying the patient's disordered breathing, such as the apnea hypopnea index (AHI) providing the number of apneas and hypopneas per hour, and the percent time in periodic breathing (% PB).

Further, metrics associated with sleep movement disorders may also be determined by the analysis unit 2020. Such metrics may include, for example, a general sleep movement disorder index (MDI) representing the number of abnormal movements arising from movement disorders such as restless leg syndrome, periodic limb movement disorder and bruxism per hour. In addition, specific indices may be calculated for each type of movement disorder, e.g., a bruxism index (BI) characterizing the number of jaw movements per hour, a RLS index (RLSI) characterizing the number of restless leg syndrome episodes per hour, and a PLM index (PLMI) characterizing the number of periodic limb movements experienced by the patient per hour.

In addition, percentage of sleep time during which the patient experiences movement disorders (% MD) may be calculated. Specific metrics relating to the percentage of time during which the patient experiences bruxism (% B), restless leg syndrome (% RLS), and periodic leg movement disorder (% PLMD) may also be determined.

Further, sleep summary metrics may be computed, either directly from the collected patient condition data, or by combining the above-listed sleep quality and sleep disorder metrics. In one embodiment, a composite sleep disordered respiration metric (SDRM) may be computed by combining the apnea hypopnea index AHI and the arousal index AI. The composite sleep disordered respiration metric (SDRM) may be computed as a linear combination of the AHI and AI as follows:

$$SDRM = c_1 * AHI + c_2 * AI \quad [1]$$

where $c_1$ and $c_2$ are constants chosen to balance the relative contributions of respiratory and arousal effects on sleep disturbance. The AHI may be monitored by performing disordered breathing detection based on transthoracic impedance measurements as previously described. The AI may be estimated, for example, by monitoring the patient activity, minute ventilation, and posture sensors for body motion indicating sleep termination or arousal. A more sensitive measure of arousal may be made using EEG signals. In this implementation, the constant $c_2$ may be adjusted to reflect the increased sensitivity to arousal.

In another embodiment, an undisturbed respiration sleep time (URST) or undisturbed respiration sleep efficiency (URSE) may be computed based on the amount of time the patient spends asleep in bed without respiratory disturbance.

The URST or URSE metrics may be determined using three parameters: total time in bed (TIB), total time asleep (TA), and combined sleep time duration in disturbed respiration (STDR). Time in bed may be determined by a combination of posture sensing and sensing the proximity of the patient to bed. The posture condition of the patient may determined, for example, using an implantable multiaxis accelerometer sensor.

The patient's total time in bed (TIB) may be determined using a proximity to bed sensor. The proximity to bed sensor may use a receiver in the sleep quality data collection and analysis unit 2020 for receiving signals transmitted from a beacon 2070 located at the patient's bed 2060. If the proximity to bed receiver detects a signal of sufficient strength from the proximity to bed beacon 2070, then the receiver detects that the patient is in bed 2060.

Total time asleep (TA) may be determined using the sleep detection method described in more detail above. The total sleep time in disturbed respiration (STDR) may be determined, for example, based on detection of sleep and disordered breathing using the sleep and disordered breathing detection methods described above.

The patient's undisturbed respiration sleep time (URST) is calculated as:

$$URST = TA - STDR \quad [2]$$

where TA=total time asleep and STDR=sleep time in disturbed breathing.

The undisturbed respiration sleep efficiency (USE) in percent is calculated $$URSE = 100 * URST/TIB \quad [3]$$

where URST=undisturbed respiration sleep time and TIB=total time in bed.

Similar metrics may be calculated for movement disorders generally, or for specific movement disorders, e.g., RLS, PLMD, or bruxism. For example, the composite RLS, PLMD, and bruxism metrics, RLSM, PLMDM, and BM, respectively, may be calculated using equations similar in form to equation 1 above:

$$RLSM = c_1 * RLSI + c_2 * AI \quad [4]$$

where RLSI=number of restless leg movement syndrome episodes per hour, AI=number of arousals per hour, and $c_1$ and $c_2$ are constants chosen to balance the relative contributions of abnormal movement and arousal effects on sleep disturbance.

$$PLMDM = c_1 * PLMDI + c_2 * AI \quad [5]$$

where PLMDI=number of periodic leg movement syndrome episodes per hour, AI=number of arousals per hour, and $c_1$ and $c_2$ are constants chosen to balance the relative contributions of abnormal movement and arousal effects on sleep disturbance.

$$BM = c_1 * BMI + c_2 * AI \quad [6]$$

where BMI=number of bruxism movement episodes per hour, AI=number of arousals per hour, and $c_1$ and $c_2$ are constants chosen to balance the relative contributions of abnormal movement and arousal effects on sleep disturbance.

The patient's undisturbed movement sleep time (UMST) and undisturbed movement sleep efficiency (UMSE) may be calculated for each movement related disorder separately or in combination using equations similar in form to equations 2 and 3, above.

In addition, a composite sleep disorder index SDI quantifying the combined effect of both respiratory and movement disorders may be computed by combining the apnea hypopnea index (AHI), the movement disorder index (MDI), and the arousal index (AI).

A sleep disturbance index (SDI) may be computed as a linear combination of the AHI, and the combined disorder index $DI_c$. The combined disorder index may include both abnormal breathing and movement components. For example, the sleep disturbance index SDI is characterizable by the equation:

$$SDI = c_4 * DI_c + c_3 * AI, \quad [7]$$

where $DI_c$ is a combined disorder index of the form:

$$DI_c = c_{41} * DI_1 + c_{42} * DI_2 \quad [7a]$$

In equation 7, $c_4$ and $c_3$ are constants chosen to balance the relative contributions of the combined disorder and arousal effects, respectively. The disorder index, $DI_c$, may be used to characterize the effects of one or more sleep disorders, including, e.g., disorders associated with disturbed respiration and/or abnormal movements. The combined disorder index may represent only one disorder index, or may be a linear combination of two or more sleep disorder indices, e.g., the apnea/hypopnea index (AHI) and the abnormal movement disorder index (MDI). The constants $c_{41}$ and $c_{42}$ may be used as weighting factors associated with particular disorder indices.

The patient's undisturbed sleep time (UST) may be calculated:

$$UST = TA - STSD \quad [8]$$

where TA=total time asleep and STSD=sleep time spent in sleep disorders.

The undisturbed sleep efficiency (USE) in percent may be calculated:

$$USE = 100 * UST/TIB \quad [9]$$

where UST=undisturbed sleep time and TIB=total time in bed.

Sleep quality metrics, such as those described above, or other metrics, may be acquired and analyzed using the sleep quality data collection and analysis unit 2020. Sleep quality metrics, in addition to raw or processed data based on physiological and non-physiological conditions may determined periodically, e.g., daily, and stored or transmitted to another device. Such data can be presented to the patient's health care professional on a real-time basis, or as a long-term, e.g., month long or year long, trend of daily measurements.

The health care professional may access the data during clinic visits via programmer interrogation of the implanted device, through occasional or periodic trans-telephonic device interrogations, or through an automatic or "on-demand" basis in the context of an advanced patient management system. The health care professionals may use the sleep quality indicator trends alone or in conjunction with other device-gathered or clinical data to diagnose disorders and/or adjust the patient's device or medical therapy as needed to improve the patient's quality of sleep.

The present invention provides diagnostic, monitoring, and evaluation capabilities relating to sleep quality and may be particularly valuable in the context of an advanced patient management system. Undiagnosed sleep disorders can lead to increased morbidity and mortality, such as those arising from various respiratory and cardiovascular consequences. Routine monitoring of patient sleep quality may lead to improved diagnosis and treatment of these syndromes and their associated co-morbidities. The invention may provide less obtrusive sleep quality monitoring, particularly and is suited for patients having an implanted device. The present invention serves to improve diagnosis of sleep disorders by reducing the inconveniences, unnatural sleep environment issues, and expenses associated with sleep clinic polysomnogram studies.

The following commonly owned U.S. patents applications, some of which have been identified above, are hereby incorporated by reference in their respective entireties: U.S. patent application Ser. No. 10/309,770, filed Dec. 4, 2002, U.S. patent application Ser. No. 10/309,771, filed Dec. 4, 2002, U.S. patent application entitled "Prediction of Disordered Breathing," identified by and concurrently filed with this patent application, U.S. patent application entitled "Adaptive Therapy for Disordered Breathing," identified by and filed concurrently with this patent application, U.S. patent application entitled "Prediction of Disordered Breathing," identified by and filed concurrently with this patent application, and U.S. patent application entitled "Therapy Triggered by Prediction of Disordered Breathing," identified by and filed concurrently with this patent application.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method for collecting sleep quality data, comprising:
sensing physiological information regarding at least one physiological condition related to sleep quality of a patient and indicative of patient sleep state;
sensing non-physiological information regarding at least one non-physiological condition that affects the sleep quality of the patient, the at least one non-physiological condition comprising an ambient condition external to the patient, the physiological information and the non-physiological information sensed contemporaneously by respective sensors;
storing the physiological information and the non-physiological information in an implantable device; and
evaluating the patient's sleep quality using both the physiological and non-physiological information by calculating a composite sleep quality metric as a function of the physiological and non-physiological information stored in the implantable device.

2. The method of claim 1, wherein the composite sleep quality metric comprises a sleep disturbance index.

3. The method of claim 1, wherein the at least one physiological condition comprises a respiratory system condition.

4. The method of claim 1, wherein the at least one physiological condition comprises a muscle system condition.

5. The method of claim 1, further comprising trending the composite sleep quality metric over time.

6. The method of claim 1, wherein the non-physiological information comprises ambient temperature.

7. The method of claim 1, wherein the at least one non-physiological condition comprises an environmental condition.

8. The method of claim 1, wherein the at least one non-physiological condition comprises a contextual condition.

9. The method of claim 1, wherein collecting the physiological information comprises collecting data associated with sleep stages.

10. The method of claim 1, wherein collecting the physiological information comprises collecting data associated with sleep disruption.

11. The method of claim 1, wherein collecting the physiological information comprises collecting data associated with disordered breathing.

12. The method of claim 1, wherein collecting the physiological information comprises collecting data associated with a movement disorder.

13. The method of claim 1, wherein collecting the non-physiological information comprises sensing the at least one non-physiological condition external to the patient and transmitting the sensed non-physiological condition to the implantable device.

14. A method for assessing sleep quality of a patient, comprising:
sensing physiological information regarding at least one physiological condition related to sleep quality of a patient using an implantable device;
sensing non-physiological information regarding at least one non-physiological condition that affects the sleep quality of the patient, the at least one non-physiological condition comprising an ambient condition external to the patient, the physiological information and the non-physiological information sensed contemporaneously by respective sensors; and evaluating the sleep quality of the patient using the physiological and non-physiological information by calculating a composite sleep quality metric as a function of the physiological and non-physiological information, wherein the evaluating the sleep quality is performed at least in part by the implantable device.

15. The method of claim 14, wherein the non-physiological information comprises patient location information.

16. The method of claim 14, wherein evaluating the sleep quality further comprises determining one or more sleep stages.

17. The method of claim 14, wherein the physiological information is indicative of sleep disruption.

18. The method of claim 14, wherein the composite sleep quality metric comprises a sleep disturbance index.

19. The method of claim 14, wherein the non-physiological information comprises ambient temperature.

20. The method of claim 14, wherein the non-physiological information is indicative of external air quality.

21. The method of claim 14, wherein evaluating the sleep quality further comprises trending the composite sleep quality metric over time.

22. The method of claim 14, wherein the physiological information is indicative of disordered breathing.

23. The method of claim 14, wherein the physiological information is indicative of one or more movement disorders.

24. The method of claim 14, wherein the non-physiological information is indicative of events that disrupt sleep.

25. The method of claim 14, wherein sensing the non-physiological information comprises sensing the at least one non-physiological condition external to the patient and transmitting the sensed non-physiological condition to the implantable device.

* * * * *